(12) United States Patent
Zychick et al.

(10) Patent No.: US 7,786,194 B2
(45) Date of Patent: Aug. 31, 2010

(54) COMPOSITIONS AND METHODS FOR PROTECTING MATERIALS FROM DAMAGE

(75) Inventors: Joel Zychick, Bethpage, NY (US); Shelby F. Thames, Hattiesburg, MS (US); Sandipan Dutta, Hattiesburg, MS (US); Sharathkumar K. Mendon, Hattiesburg, MS (US); Oliver W. Smith, Petal, MS (US)

(73) Assignee: AgroShield, LLC, New Orleans, LA (US)

( * ) Notice: Subject to any disclaimer, the term of this patent is extended or adjusted under 35 U.S.C. 154(b) by 902 days.

(21) Appl. No.: 10/594,470

(22) PCT Filed: Apr. 2, 2004

(86) PCT No.: PCT/US2004/010339
§ 371 (c)(1),
(2), (4) Date: Sep. 27, 2006

(87) PCT Pub. No.: WO2005/105870
PCT Pub. Date: Nov. 10, 2005

(65) Prior Publication Data
US 2007/0155865 A1 Jul. 5, 2007

(51) Int. Cl.
*C08L 89/00* (2006.01)
*C09J 189/00* (2006.01)
(52) U.S. Cl. .................................. 524/25; 524/560
(58) Field of Classification Search .............. 524/25, 524/560
See application file for complete search history.

(56) References Cited

U.S. PATENT DOCUMENTS

| | | | |
|---|---|---|---|
| 2,509,857 A | 5/1950 | Borcherdt |
| 2,579,451 A | 12/1951 | Polson |
| 2,812,317 A | 11/1957 | Barrett |
| 2,861,059 A | 11/1958 | Mowry |
| 3,200,102 A | 8/1965 | Kleiner |
| 3,563,461 A | 2/1971 | Cole |
| 3,584,412 A | 6/1971 | Palmer |
| 3,615,972 A | 10/1971 | Morehouse |
| 3,709,842 A | 1/1973 | Stoy |

(Continued)

FOREIGN PATENT DOCUMENTS

JP 56040758 4/1981

(Continued)

OTHER PUBLICATIONS

Pelton, "Preparation of Aqueous Latices with N-Isopropylacrylamide", May 4, 1986, Colloids and Surfaces, V20, pp. 247-256, Elsevier Science, Amsterdam.

(Continued)

*Primary Examiner*—Satya B Sastri
(74) *Attorney, Agent, or Firm*—Michael Haynes PLC; Michael N. Haynes

(57) ABSTRACT

Certain exemplary embodiments comprise a composition prepared from a Class 1 member, a Class 2 member, and a Class 3 member, said Class 1 member contributing approximately 0.1 percent to approximately 10 percent by dry weight of said composition, said Class 2 member contributing approximately 1 percent to approximately 10 percent by dry weight of said composition, and said Class 3 member contributing an amount up to a balance by dry weight of said composition.

33 Claims, 13 Drawing Sheets

63% MMA/27% BA/3% DVB
Internally crosslinked nanoparticles (d = 230 nm)

U.S. PATENT DOCUMENTS

| | | |
|---|---|---|
| 3,864,323 A | 2/1975 | Stoy |
| 3,897,382 A | 7/1975 | Stoy |
| 4,161,084 A | 7/1979 | Arny |
| 4,183,884 A | 1/1980 | Wichterle |
| 4,352,458 A | 10/1982 | Masel |
| 4,363,760 A | 12/1982 | Cioca |
| 4,419,288 A | 12/1983 | Cioca |
| 4,732,930 A | 3/1988 | Tanaka |
| 4,748,220 A | 5/1988 | Hartmann |
| 4,963,656 A | 10/1990 | Mitani |
| 4,975,375 A | 12/1990 | Haruta |
| 5,052,618 A | 10/1991 | Carlon |
| 5,082,177 A | 1/1992 | Hill |
| 5,183,879 A | 2/1993 | Yuasa |
| 5,185,024 A | 2/1993 | Siemer |
| 5,225,062 A | 7/1993 | Yoshioka |
| 5,270,055 A | 12/1993 | Moest |
| 5,285,769 A | 2/1994 | Wojcicki |
| 5,653,054 A | 8/1997 | Savignano |
| 5,668,082 A | 9/1997 | Miller |
| 5,672,656 A | 9/1997 | Murayama |
| 5,985,573 A | 11/1999 | Hennink |
| 6,057,266 A | 5/2000 | Colvin |
| 6,097,530 A | 8/2000 | Asher |
| 6,180,562 B1 | 1/2001 | Blum |
| 6,199,318 B1 | 3/2001 | Stewart |
| 6,794,436 B2 | 9/2004 | Schlarb |
| 2001/0027072 A1 | 10/2001 | Mumick |
| 2003/0054170 A1 | 3/2003 | Fujimoto |
| 2003/0103927 A1 | 6/2003 | Maubru |
| 2003/0177868 A1 | 9/2003 | Guillet |
| 2003/0232914 A1* | 12/2003 | Devonport et al. .......... 524/501 |

FOREIGN PATENT DOCUMENTS

| | | |
|---|---|---|
| JP | 61-015626 | 1/1986 |
| JP | 61148278 | 7/1986 |
| JP | 03-000701 | 1/1991 |
| JP | 05-262882 | 10/1993 |
| JP | 10077201 | 3/1998 |
| JP | 2000178398 | 6/2000 |
| JP | 2001-261845 | 9/2001 |
| JP | 2001-524946 | 12/2001 |
| JP | 2003-064299 | 3/2003 |
| JP | 2004027226 | 1/2004 |
| KR | 20010095367 A | 11/2001 |
| WO | WO9838867 | 9/1998 |
| WO | WO/00/42843 | 7/2000 |
| WO | WO0170022 | 9/2001 |
| WO | WO01/90226 | 11/2001 |
| WO | WO02/092652 | 11/2002 |
| WO | WO/2004/030455 | 4/2004 |

OTHER PUBLICATIONS

Topp, "Thermosensitive Micelle-Forming Block Copolymers of Poly(ethylene glycol) and Poly(N-Isopropylacrylamide)", Jul. 18, 1997, American Chemical Society, Macromolecules, V.30, N. 26, pp. 8518-8520.

Feil, "Critical Solution Temperature of N-Isopropylacrylamide Copolymers", May 1, 2002, Macromolecules, 1993, 26, pp. 2496-2500.

O'Callaghan, "Mixed Initiator Approach to the Surfactant-Free Semicontinuous Emulsion Polymerization of Large MMA/BA Particles", Journal of Applied Polymer Science, May 23, 1995, pp. 2047-2055, vol. 58, Journal of Applied Polymer Science, vol. 58, John Wiley & Sons, Inc.

* cited by examiner

63% MMA/27% BA/3% DVB

Internally crosslinked nanoparticles (d ≈ 230 nm)

|  | AG 46 | | AG 46A | | AG 47B | | AG 50 | | AG 14R | |
|---|---|---|---|---|---|---|---|---|---|---|
|  | 0.53 | 2.70 | 0.59 | 2.56 | 0.53 | 2.70 | 0.41 | 2.22 | 0.44 | 2.14 |
| DI water | 150 | 80.21 | 130 | 76.92 | 150 | 80.21 | 200 | 81.63 | 180 | 79.42 |
| NAHCO₃ | 0 | 0.00 | 2 | 1.18 | 0 | 0.00 | 0 | 0.00 | 1.65 | 0.73 |
| CD 571 | 25 | 13.37 | 25 | 14.79 | 25 | 13.37 | 30 | 12.24 | 20 | 8.82 |
| Acrylamide | 5 | 2.67 | 5 | 2.96 | 0 | 0.00 | 0 | 0.00 | 7 | 3.09 |
| NIPAM | 0 | 0.00 | 0 | 0.00 | 5 | 2.67 | 5 | 2.04 | 0 | 0.00 |
| Acrylic acid | 3 | 1.60 | 3 | 1.78 | 3 | 1.60 | 5 | 2.04 | 2 | 0.88 |
| APS | 2 | 1.07 | 2 | 1.18 | 2 | 1.07 | 2 | 0.82 | 2 | 0.88 |
| PPG diacrylate | 2 | 1.07 | 2 | 1.18 | 2 | 1.07 | 3 | 1.22 | 1 | 0.44 |
| TRG monomer | 0 | 0.00 | 0 | 0.00 | 0 | 0.00 | 0 | 0.00 | 10 | 4.41 |
| Tween 80 | 0 | 0.00 | 0 | 0.00 | 0 | 0.00 | 0 | 0.00 | 3 | 1.32 |
|  | 187 | 100.00 | 169 | 100.00 | 187 | 100.00 | 245 | 100.00 | 226.65 | 100.00 |

FIG. 7

COMPOSITIONS AND METHODS FOR PROTECTING MATERIALS FROM DAMAGE

BRIEF DESCRIPTION OF THE DRAWINGS

The claims and their wide variety of potential embodiments will be more readily understood through the following detailed description, with reference to the accompanying drawings in which:

FIG. 7 is a table listing exemplary polymer compositions; and

DEFINITIONS

Figure 1:
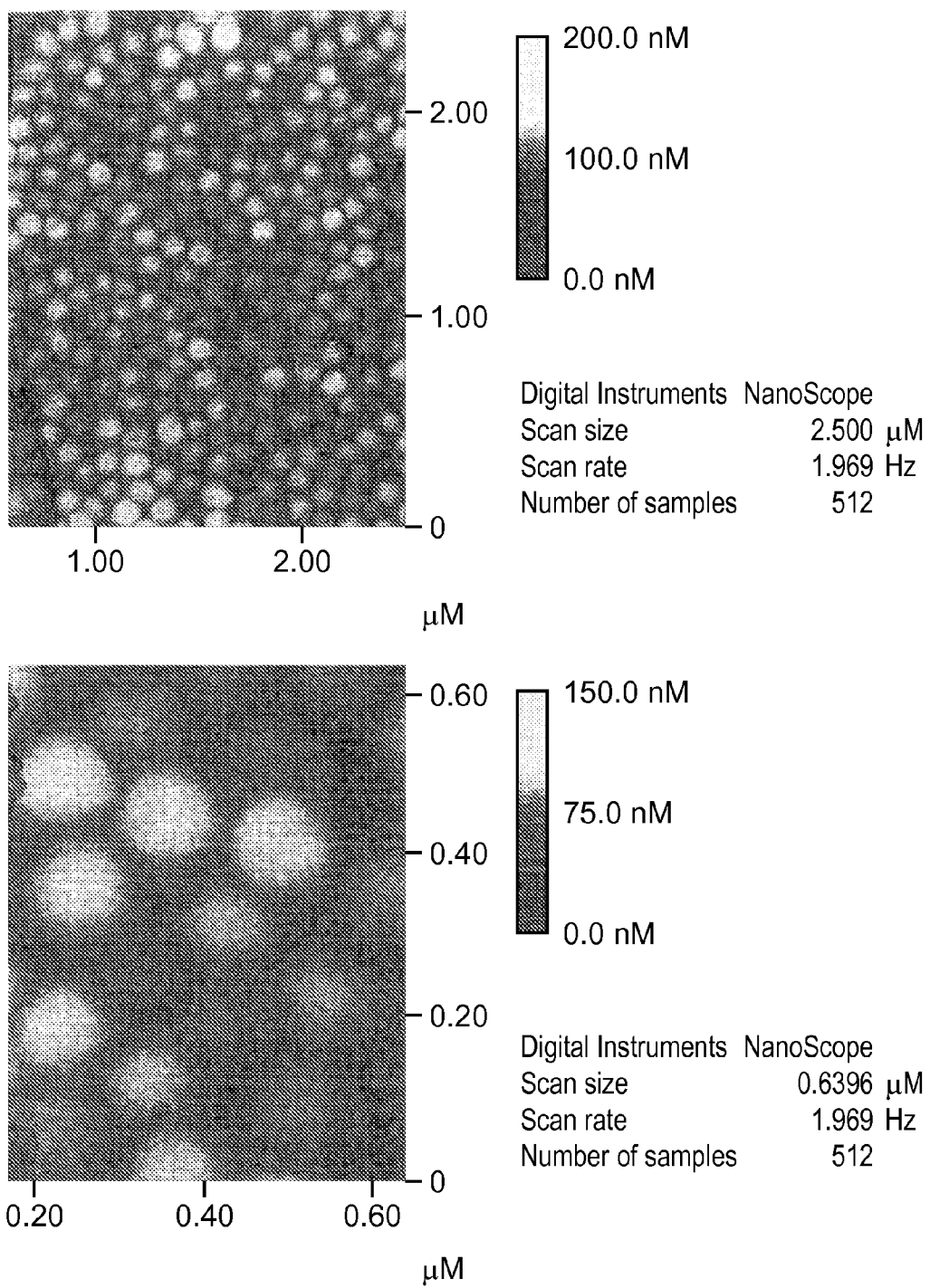
FIG. 1 is a photograph of an atomic force microscope image of internally cross-linked nanoparticles.

When the following terms are used herein, the accompanying definitions apply:

ambient temperature—a temperature of an environment contacting and/or surrounding an object or composition of interest. For example, the temperature of air contacting a surface.

Class 1—a multifunctional hydrophilic monomer with 2 or more functionalities, and comprising at least 2 acrylic groups but less than 5 acrylic groups and not more than 11 hydroxyl groups. Examples include: hydrophilic acrylates/methacrylates with at least 2 acrylic/methacrylic groups, such as diacrylate, propoxylated neopentyl glycol diacrylate (commercially available from Sartomer Corporation under the tradename SR 9003), alkoxylated diacrylate, ethoxylated bisphenol diacrylate (commercially available from Sartomer corporation under the tradename SR 480), and pentaerythritol triacrylate.

Class 2—a processing aid. Examples include: thermally activated free radical polymerization initiators, ultraviolet activated free radical polymerization initiators, surfactants, and other processing aids such as mold release agents. Further examples include: $C_6H_5COC_6H_4$(p-$CH_2NMe_2Cl$—$CH_2CH_2OCOCHCH_2$)(commercially available under the tradename Quantacure); $C_6H_5COC_6H_4$(p-$(OCH_2CH_2)_4OCOCHCH_2$) (commercially available from the UCB Group under the tradename Uvecryl); acetyl peroxide (commercially available from Aldrich), azo bisisobutyronitrile (commercially available from Aldrich); benzoyl peroxide (commercially available from Aldrich); cumene hydroperoxide (commercially available from Aldrich); ammonium persulfate; potassium persulfate; soybean protein; Irgacure 2959 (commercially available from Ciba); and Tween 80 (commercially available from ICI).

Class 3—a monofunctional acrylate or methacrylate having a molecular weight of more than 50 and less than 500. Examples include: propylene glycol methacrylate (molecular weight (MW)=144), acrylic acid (MW=72), N-isopropyl acrylamide, acrylamide, polyethylene glycol monomethacrylate (MW=400), trimethylol propane monoacrylate (MW=188), ethoxylated polyoxymethylene glyceryl monomethacrylate (MW=600), ethoxylated hydroxyethyl methacrylate (commercially available from Sartomer Corporation under the tradename CD-571), and fatty acid modified epoxy acrylate (available commercially from Sartomer Corporation under the tradename CN 2101).

coating—the act of applying a first material to at least a portion of a surface of a second material. In some cases, upon application, a mechanical, physical, and/or chemical attachment, bond, and/or interaction can form between the materials. Examples include conventional coating processes such as spraying or dipping; vacuum deposition techniques; and such surface-modification technologies as diffusion, laser and plasma processes, chemical plating, grafting or bonding, hydrogel encapsulation, and bombardment with high-energy particles.

dry weight—a weight of a non-hydrated composition.

gel—a cross-linked polymer.

heat—a form of energy associated with the motion of atoms or molecules and capable of being transmitted by conduction, convection, and/or radiation.

nanoparticle—a solid particle with an average major diameter of from about 2 nanometers to about 1000 nanometers, including all values and all subranges therebetween.

plant—organisms of the kingdom Plantae, whether unharvested or harvested. Examples include crops, grains, tobacco, trees, nuts, flowers, vegetables, fruits, berries, and/or produce, etc.

plant material—any portion of a plant, including the entire plant. Examples include seeds, seedlings, sprouts, sprigs, roots, bark, branches, stems, buds, leaves, flowers, fruit, and/or other parts of the plant.

solid particle—a particle that is not hollow.

surface—the outer boundary of an object or a material layer constituting or resembling such a boundary.

total weight—a weight of a hydrated composition.

DETAIL DESCRIPTION

Certain exemplary embodiments of compositions, and methods of applying the compositions to materials, are disclosed. Certain exemplary embodiments can provide a composition comprising water droplets comprising a dispersion of particles comprising a polymer comprising at least one hydrophobic component and at least one hydrophilic component. The polymer can release heat over a range of ambient temperatures, including dropping, stable, and/or rising ambient temperatures, an upper bound of the range about 5° C. and a lower bound of the range about −15° C., including all values and subranges therebetween. The polymer can be formed from polymerization and/or copolymerization. The composition, when applied to at least a portion of a surface of a material, can reduce damage to the material, and/or can effectively reduce the threshold temperature at which substantial ice formation, frost damage, and/or freeze damage to the material will occur.

Certain exemplary embodiments can be useful for the protection of plant materials (e.g., crops, grains, tobacco, trees, nuts, flowers, vegetables, fruit, berries, and/or produce, etc.) and/or any portion thereof (e.g., seeds, seedlings, sprouts, sprigs, roots, bark, branches, stems, buds, leaves, flowers, fruit, and/or other parts of the plant) from damage via the application of an aqueous spray of specially formulated polymer and/or copolymer mixtures which can form coatings which cover the plant materials.

The coatings can be non-toxic and/or can transmit gases such as oxygen and/or carbon dioxide to and/or from the plant, but can restrict the evaporation of water from the plant which might otherwise cause the plant to cool, dry and/or shrink. The polymer (plastic) coating can undergo an exothermic phase change below, at, or slightly above the freezing point of water, which can supply heat to the coated parts of the plant.

The polymers can be soluble, swellable, and/or dispersible in water, and/or the water dispersion can have a relatively low viscosity so that it can be readily sprayed in conventional commercial spray systems.

While not being bound by any particular theory, it is believed that heat can be released over a temperature range because the polymers and/or copolymers in certain exemplary compositions can exhibit a phase change within and/or over a range of from about 5° C. to about −15° C., including all values therebetween, including for example about 4.44, 3, 2.15, 0.9, 0.1, −1.3, −2, −3.1, −4.99, −6.01, −9.9, −14.6° C. etc., and including all subranges therebetween, including from about 3° C. to about −14° C., from about 1° C. to about −1° C., from about 0° C. to about −5° C., etc.

Much of the heat released from such exemplary polymers and/or copolymers can be transferred to the plant body, which thereby can be protected from freezing. The coating layer might also insulate the plant, so that the transferred heat can be more effectively retained within the plant.

Additionally, it is believed that certain exemplary compositions might also have the ability to depress the freezing point of water that might condense and/or collect on the plant and/or other surfaces subsequent to application of the composition to the plant and/or other surface.

Regardless of the actual mechanism of their operation, certain exemplary compositions can be applied such that at least a portion of the plant surface is coated with the composition. Application of the compositions is not limited to any particular type of plant or to any particular stage of development of the plant or to any particular portion of the plant. Thus, certain exemplary compositions can be applied to any plant, at any stage in its development, and to any portion thereof that might benefit from protection from frost and/or freeze. Such plants include, for example, any conventional agricultural crop that may be intended for human and/or animal consumption such as fruits, vegetables, grass, hay, and so forth, or to plants grown for other purposes including, but not limited to, ornamentation, including flowers and shrubs, forestation development, erosion protection, diverse industrial applications, and so forth.

Certain exemplary compositions can be applied to plants that are immature, e.g, sprouts, seedlings, and so forth, as well as to more mature plants, e.g., those that are budding, fruit-bearing, foliage-bearing, and so forth.

Furthermore, certain exemplary compositions are not limited to application to growing plants. Thus, certain exemplary compositions can be applied to plants, or any portion thereof, that have been severed from the land, but that are still subject to environmental conditions that may result in frost and/or freeze damage thereto.

Certain exemplary compositions can be applied to the plants in any manner that results in at least a portion of the plant surface being coated with the compositions. Thus, there is no limitation to any particular mode of application. Hence any conventional method used to contact plants with liquids, semi-liquids, gels, solids, and so forth, may be employed. For example, certain exemplary compositions can be applied by spraying, for example, via nozzles or sprinkling systems, by broadcasting, dousing, soaking, and so forth using any conventional method or apparatus.

Certain exemplary compositions can be applied in the form of an aqueous solution. For example, in the case of a hydrated polymer gel, an aqueous solution of the hydrated polymer gel may be applied.

Certain exemplary compositions can also be applied in the form of water droplets coated with a polymer (e.g., microcapsules). The polymer coating the water droplets can be a hydrated polymer gel. Such coated water droplets can be formed by any conventional method including microencapsulation techniques in which water droplets are coated with a layer of a polymer. Microencapsulation is a technique for providing a thin coating on typically micron-sized particles, that may be liquid, solid, semi-solid, and so forth. A microencapsulation technique that can be used to produce coated water droplets can involve forming a mist of water droplets using an atomizing spray gun or an ultrasonic nozzle, then intersecting the stream of droplets with an orthogonal stream of droplets of the hydrated gel solution.

Other methods of forming water droplets coated with a polymer can include, for example, forming a suspension of water with a nonaqueous solution (e.g. a suspension) of the hydrated gel, then spraying the suspension through a fine nozzle. A volatile polar liquid immiscible with water can form a suspension that develops a micellar structure when water is added to the solution (or suspension) of the hydrated gel in this liquid. Polar liquids useful in this method include, for example, acetonitrile, 1-hexanol, and isopropyl ether, etc. Upon spraying, the polar liquid can be evaporated.

Prior to application of the coating layer, the size of the water droplets to be coated with a polymer can range from about 0.1 mm to about 1.0 mm, including all values therebetween, and including all subranges therebetween, such as from about 0.3 to about 0.95 mm. The thickness of the polymer layer coating the water droplets may range from about 100 microns to about 500 microns, including all values therebetween, and including all subranges therebetween, such as for example, from about 300 microns to about 500 microns.

When applying coated water droplets to plants, the coated water droplets can be applied first, followed by an aqueous solution of the polymer. However, this sequence can be reversed. By repeated application of coated water droplets and aqueous solution of the polymers, multiple layers can be achieved. By applying the composition in the form of coated water droplets, a plant to be coated with an effectively greater reservoir of water than would be the case if only the aqueous solution were applied to the plant. Moreover, in certain scenarios, it might be undesirable to include too much water in a hydrated polymer gel since the gel might become fragile and/or might lose its desired behavior of freezing over a wide temperature range. Thus, the additional water provided by the water droplets obviates using a polymer that is so hydrated that its efficacy is substantially reduced. Without being held to any particular theory of operation, it is believed that hydrogen bonding of the water encapsulated within the polymeric coating layer stabilizes the encapsulated water droplet, slows down evaporation of the water, and/or allows the coating to retain its structural integrity through several days of use.

Certain exemplary polymers used to coat the water droplets include the polyacrylic acid and polyamino acid gels that are described below.

Certain exemplary compositions can also be applied in the form of a foam. When applied as a foam, the polymer can be used to entrap air bubbles to form a stable foam. It is believed that the inner and outer surfaces of the polymer undergo cross-linking through hydrogen bond formation, adding structural integrity to the foam. The foam can be formed by any conventional means, e.g., by creating air bubbles of controlled sized in a solution of the polymer gel which can lead to a stable suspension of air bubbles coated with the gel. The foam thus formed can be applied by any of the methods discussed above, including by spraying. The foam can be substantially transparent or reflective, depending on the size of the air bubbles enclosed by the polymer and/or the water content of the gel. The gel can have a water content in the range of from about 50 percent to about 90 percent by weight, including all values and all subranges therebetween. The average diameter of the air bubbles in the foam can be in the range of from about 10 to about 100 microns. A foam having such air bubbles can reflect about 3 percent of the visible radiation incident upon it, provided that the polymer gel has a water content of about 70 percent by weight, and the dry polymer has a refractive index about 1.50. Certain exemplary polymers can have a refractive index of the dry polymer in the range of from about 1.40 to about 1.60.

Certain exemplary foams can be used in conjunction with the aqueous solution and coated water droplet forms of the composition. Thus, for example, a first layer of coated water droplets may be applied to a plant surface, followed by a layer of the aqueous solution, followed by a foam layer. It is to be understood that this sequence is merely exemplary and other sequences may be used, and multiple layers may thus be formed.

Certain exemplary compositions, when applied to at least a portion of a plant surface, can provide frost protection for several days before potentially losing efficacy due to dehydration caused by evaporation of the water molecules associated with the polymers. Even upon evaporative loss of the water molecules, it is believed that certain exemplary polymers can maintain their integrity as coatings by reorganizing their structure. Thus, certain exemplary polymers can continue to provide insulative protection to the plant, despite potentially gradually losing their ability to release heat upon encountering freezing conditions. Moreover, certain exemplary polymers can regenerate their ability to release heat upon encountering freezing conditions by being remoisturized, for example, by exposure to humid conditions, particularly rain, or if the plant is irrigated.

Certain exemplary compositions can comprise a polymer component that enhances the ability of the composition to adhere to the surface of the plant and/or to form relatively thin and/or uniform coatings on the surface of the plant. Thus, certain exemplary compositions can provide optimal frost and/or freeze protection. In certain exemplary compositions, the polymer and water associated therewith can be applied to the plant in an amount to provide a coating comprising from about 0.5 percent to about 3 percent of the weight of the plant material to be coated. In certain exemplary applications, the gel material can comprise about 30 percent of the weight of the coating. Thus, the gel material can comprise from about 0.15 percent to about 0.9 percent of the weight of the plant material to be coated. In a coating application where the coating comprises 1 percent of the weight of the plant material, the gel material can comprise 0.3 percent of the weight of the plant material.

Desired weight percentages can be obtained when certain exemplary compositions form a coating having a thickness in the range of from about 200 microns to about 1000 microns, including all values and subranges therebetween. These weight and thickness ranges are merely exemplary. Thus, application of a greater weight of coating material relative to the weight of the plant body, hence a greater coating thickness, can provide greater protection against frost and/or freeze. For example, a coating that is applied at a 2 percent level relative to the weight of the plant material can release approximately twice as much heat as would a coating applied at a 1 percent level. Thus, greater levels of heat can be released and a greater level of protection can be afforded when the higher coating levels are used. Extra protection may be desired, for example, when a longer spell of freezing conditions is expected or when protection is desired over a larger temperature range of the ambient air.

Certain exemplary compositions can include other components, such as components that are non-toxic to humans, biodegradable, water soluble, water insoluble, etc., in addition to the polymer. For example, the compositions may include one or more components such as micronutrients, macronutrients, pesticides, insecticides, herbicides, rodenticides, fungicides, biocides, plant growth regulators, fertilizers, microbes, plant growth regulators, soil additives, adhesion promoting-agents, surfactants, freezing point modifiers, and/or ultraviolet light absorbers, etc. Thus, certain exemplary compositions can include virtually any additional component(s) that is/are conventionally used in the treatment of plants, including additional components that are non-toxic to humans, biodegradable, water soluble, and/or water insoluble, etc. In addition, the compositions can include components used for the treatment of soil, such as fertilizers, soil amendments, and/or pesticides, etc. Thus, certain exemplary compositions can function as carriers for such additional components that may be dispersed, dissolved, and/or otherwise incorporated within the compositions or any distinct phase or portion of such compositions.

Certain exemplary compositions can include other additives that enhance and/or alter the properties of the coating per se without necessarily deleteriously affecting the broad freezing range of such compositions. Such additives can be non-toxic to humans, biodegradable, water soluble, and/or water insoluble, etc. For example, freezing point modifiers, such as freezing point depressants, can be added to certain exemplary compositions to further reduce the freezing temperature of those compositions. Such freezing point depressants include, for example, monohydric alcohols, small chain dihydroxy and polyhydroxy alcohols such as propylene glycol, among others, and/or polyalkylene glycols such as polyethylene glycol and polypropylene glycol, etc.

Surfactants (also known in the art as spreaders, film extenders, and/or wetting agents) such as nonionic, cationic, anionic and/or amphoteric surfactants, can be included within certain exemplary compositions, including surfactants that are non-toxic to humans, biodegradable, water soluble, and/or water insoluble, etc. Certain ionic surfactants, for example, when added to certain exemplary compositions, can promote cross-linking of the polymers and hence promote a more stable coating layer. On the other hand, certain nonionic surfactants, when added to certain exemplary compositions, can help to prevent clumping of the polymer thus facilitating a more uniform coating layer. Polyhydric alcohols can be added to an aqueous solution of certain exemplary polymer gels in order to reduce the surface energy of the hydrated gel particles. Examples of polyhydric alcohols that can be used include, for example, small chain dihydroxy and polyhydroxy alcohols such as ethylene glycol and propylene glycol, among others, and/or polyalkylene glycols including polyethylene glycol and polypropylene glycol, among others. By thus reducing the surface energy of the hydrated gel particles, surface wetting, and/or coverage can be increased.

Surfactants may be used to increase the resistance of a component added to certain exemplary compositions from being removed by rain, dew, and/or irrigation. Anionic surfactants also can be helpful in preventing such additives from being readily absorbed through plant cuticles, and thus can be used when it is desired for the additive to remain on the outer surface of the plant. Non-ionic surfactants, on the other hand, can be useful when it is desired to increase the transport of such an additive through plant cuticles, and therefore can be used with systemic herbicides, nutrients, and the like.

Certain exemplary compositions can include one or more substances that improve the adhesion of the composition, or any component within the composition, to a surface of a plant or other material. Such adhesion-promoting substances are known in the art as "stickers", and can be non-toxic to humans, biodegradable, water soluble, water insoluble, etc. Stickers, for example, can improve the adhesion of finely-divided solids or other water-soluble or -insoluble materials to plant and/or surfaces. Thus, stickers can improve resistance of a material provided as a coating to a surface to the effects of time, wind, water, mechanical, and/or chemical action, etc. For example, a sticker can improve the adhesion of a pesticide added to certain exemplary compositions against wash-off due to rainfall, heavy dew or irrigation, and also help prevent pesticide loss from wind or leaf abrasion. It is to be understood that, when added to certain exemplary compositions, stickers can improve the adhesion properties that can be inherently present in those compositions by virtue of the polymer component therein.

Certain exemplary compositions can include one or more ultraviolet light absorbers, which can enhance the heat creation ability of the polymer.

Certain exemplary compositions can comprise polymers that release heat over a range of ambient temperatures having an upper bound of about 1.7° C. One example of a polymer that releases heat over a range of ambient temperatures beginning at about 1.7° C. is a hydrolyzed polyacrylonitrile. Upon hydrolysis of polyacrylonitrile by a strong base, such as an aqueous solution of sodium hydroxide, it is believed that a copolymer of acrylamide and acrylic acid is formed. This copolymer is a water-soluble, uncross-linked polyacrylamide-acrylic acid gel that is believed to be held together by hydrogen bonds. It is believed that the polymer gel has a hydration shell surrounding the polymer chain and that the hydration shell helps to keep the polymer in aqueous solution. A slightly acidic pH range of the aqueous solution facilitates maintaining the polymer in aqueous solution. A pH of the aqueous solution of from about 5 to about 7 can be maintained in order to keep the polymer in solution. The polyacrylamide-acrylic acid gel thus formed can be hydrated to a water content in the range of from about 70 weight percent to about 90 weight percent. As discussed above, gels having a higher water content can become fragile and/or can lose their desired freezing behavior occurring over a wide temperature range.

Certain exemplary polymers can be substantially uncrosslinked, have a relatively low amount of crosslinking, have a high degree of crosslinking, and/or be substantially crosslinked. Certain exemplary polymers can exhibit a broad freezing point transition.

The following United States Patents are incorporated by reference herein in their entirety: U.S. Pat. No. 2,579,451 (Polson), U.S. Pat. No. 2,812,317 (Barrett), U.S. Pat. No. 2,861,059 (Mowry), U.S. Pat. No. 3,200,102 (Kleiner), U.S. Pat. No. 3,563,461 (Cole), U.S. Pat. No. 3,584,412 (Palmer), U.S. Pat. No. 3,615,972 (Morehouse), U.S. Pat. No. 3,709,842 (Stoy), U.S. Pat. No. 3,864,323 (Stoy), U.S. Pat. No. 3,897,382 (Stoy), U.S. Pat. No. 4,161,084 (Arny), U.S. Pat. No. 4,183,884 (Wichterle), U.S. Pat. No. 4,352,458 (Masel), U.S. Pat. No. 4,363,760 (Cioca), U.S. Pat. No. 4,419,288 (Cioca), U.S. Pat. No. 4,963,656 (Mitani), U.S. Pat. No. 5,052,618 (Carlon), U.S. Pat. No. 5,082,177 (Hill), U.S. Pat. No. 5,185,024 (Siemer), U.S. Pat. No. 5,285,769 (Wojcicki), U.S. Pat. No. 5,653,054 (Savignano), U.S. Pat. No. 5,668,082 (Miller), U.S. Pat. No. 6,057,266 (Colvin), U.S. Pat. No. 6,180,562 (Blum).

An exemplary polymer can be a hydrolyzed product of a fibrous protein such as, for example, fibrin, fibronectin, and/or elastin. Such hydrolyzed fibrous protein products can be prepared by known methods, such as enzymatic hydrolysis with an enzyme such as elastase, pepsin, and/or pronase and by nonenzymatic processes including, for example, acid and alkaline hydrolysis. It is believed that the hydrolysis product of these fibrous proteins is a polymer comprising polyamino acid moieties (i.e. polypeptides) and acrylamide moieties. An exemplary hydrolyzed fibrous protein product is a polyamino acid/polyacrylamide copolymer.

Other polymers that can be useful include, for example, polyols such as those prepared from partial hydrolysis of polysaccharides including, but not limited to starch, cellulose, and/or derivatives thereof including, e.g., hydroxypropyl methylcellulose, hydroxypropyl cellulose, and carboxymethyl cellulose. Hydroxypropyl methylcellulose can be prepared by reacting a purified form of cellulose obtained from, e.g., cotton waste or wood pulp with sodium hydroxide solution to produce a swollen alkali cellulose which then can be treated with chloromethane and propylene oxide to produce methylhydroxypropyl ethers of cellulose. The partial hydrolysis of these and other polysaccharides can be carried out by conventional processes including, e.g., alkaline or acid hydrolysis.

Certain exemplary hydrolyzed polyacrylonitriles that may be used in the certain exemplary compositions can be prepared by known methods, including both acid and alkaline hydrolysis of polyacrylonitriles to form a polymer containing acrylamide and acrylic acid moieties. An exemplary method involves hydrolyzing polyacrylonitrile by a strong base such as an aqueous solution of sodium hydroxide to produce a substantially uncrosslinked and water-soluble polyacrylamide-acrylic acid gel that is believed to be held together by hydrogen bonds. While, as discussed above, the alkaline hydrolysis product can contain both acrylamide and acrylic acid moieties, it can also contain some unhydrolyzed acrylonitrile moieties.

Polyacrylonitrile can be hydrolyzed to produce a random copolymer of acrylamide and acrylic acid. The relative ratio of acrylamide and acrylic acid can be largely dependent on the hydrolysis conditions. Control of these compositions can also be obtained by direct copolymerization of acrylic acid and acrylamide, both of which are commercially available Such polymer and copolymer mixtures can be delivered as a dispersion of internally crosslinked particles that have relatively low viscosity in water and/or are relatively easy to deliver in water spray. Such polymers can be prepared by the method described by O' Callaghan et al. (Journal of Polymer Science A, vol. 33, page 1849, 1995), which is incorporated herein by reference in its entirety. Each of the resulting particles can be internally-crosslinked. Each of the particles can be a substantially solid particle. Each of the particles can have a molecular weight of from about five hundred thousand (500,000) to about fifty million (50,000,000), including all values therebetween and all subranges therebetween. Each particle can be a nanoparticle. FIG. 1 is a photograph of an atomic force microscope image of internally cross-linked nanoparticles, formed via activities described herein, the nanoparticles having an average diameter of about 230 nanometers.

EXAMPLE 1

Preparation of an Internally Crosslinked Polymer Dispersion

To prepare a fine polymer suspension and/or dispersion by surfactant-free emulsion polymerization, the following procedure was followed. In a three-necked, 1-L round-bottom flask (flask A) fitted with a condenser with a nitrogen inlet, a mechanical stirrer and a rubber septum, 220 mL of deionized water was placed. The flask was placed into a water bath with a temperature controller set to 80° C. The bath was turned on and nitrogen was bubbled through the deionized water of the flask for ca. 1.5 h. When the temperature of the water bath reached 80° C. (in about 1.5 h), a solution of ammonium persulfate (1.0 g) in 20 mL deionized water was added to flask A. The nitrogen inlet was removed temporarily from flask A and inserted in another flask (flask B) where a monomer mixture was prepared under a nitrogen blanket. The nitrogen was used to remove air from the flask, the pump, and the connecting tubes by flowing the nitrogen therethrough for about 3 to 5 minutes.

The monomer mixture of flask B contained 180 mL of water, 20 g of N-isopropylacrylamide (NIPAM) monomer, 3.72 mL of acrylonitrile monomer, and 0.6 g (2.5 percent on monomers) of N,N-methylene-bis-acrylamide monomer, which functioned as a cross-linker. Then the monomer mixture of flask B was slowly pumped (at a rate of 6 mL/min) from flask B into flask A in a nitrogen atmosphere. During the continuous addition of the contents of flask B to flask A, rapid polymerization created a polymer of substantially uniform concentration, the polymer an internally crosslinked copolymer of NIPAM and acrylonitrile, the polymer present in the water as a dispersion of particles. After monomer addition was completed, the contents of flask A were allowed to react for a further 2 h at 80° C. Throughout the polymerization within flask A, the reaction mixture was stirred at 300 rpm. All the monomers and other reagents were purchased from Aldrich, Caledon, or Eastman, and used without any additional purification.

In certain exemplary embodiments, NIPAM can be copolymerized with a hydrophobic monomer such as, for example, acrylonitrile, methyl methacrylate, and/or styrene, etc. Poly(NIPAM) goes through a reversible phase transition at 31° C. Cooling this polymer in water solution or dispersion would give off heat at this temperature. However, copolymerization of NIPAM with a hydrophobic monomer can reduce the temperature at which this phase transition would occur to closer to 0° C., or the freezing point of water. By carefully controlling the ratio of NIPAM to the hydrophobic monomer, the precise temperatures at which this phase transition occurs can be controlled. Moreover, by creating a mixture of more than one copolymer with varying amounts of one or more hydrophobic monomers, a broad range of phase transition could release heat over a wide range of temperatures at or near 0° C. This would then result in a wider range of frost protection for plants or crops at, above, and below the freezing point of water.

In addition, multiple polymers and/or copolymers can be provided, each releasing heat over different temperature ranges. For example, a first copolymer can release heat over a range of ambient temperatures of about 5° C. to about 0° C. A second copolymer can release heat over a range of ambient temperatures beginning at about 1° C. to about −4° C. Additional copolymers can be designed, included in an aqueous solution, and applied to plants as desired to achieve different heat producing effects at various temperature ranges of interest. Thus, certain polymers and/or copolymers can protect against light or short freezes, other polymers and/or copolymers can protect against deeper or longer freezes, etc. Likewise, as desired, certain polymers and/or copolymers can be selected, produced, and/or applied to provide differing insulating properties, differing evaporative loss properties and/or differing mass transfer properties.

As mentioned above, the relative amount of hydrophobic monomer may be varied to change the temperature at which the copolymer undergoes phase transition and releases heat. In certain exemplary embodiments, mixtures can be formed that include varying amounts of copolymer whereby the copolymers in the mixture contain a different amount of a specific hydrophobic monomer. For example, the hydrophobic monomer can make up from about 1 percent to about 50 percent by dry weight of the copolymer, including all values and all subranges therebetween, including from about 10 percent to about 40 percent, from about 20 percent to about 39.9 percent, and/or from about 20.1 percent to about 30.2 percent of the copolymer used in the mixture.

While two specific examples have been discussed herein, other combinations of polymers are possible and considered within the scope of the attached claims. Moreover, other ratios of hydrophobic monomers are possible and would be within the scope of the attached claims. In some cases it might be desirable to include some high molecular weight, uncrosslinked water-soluble polymers to aid in the adhesion of the coating to the plant surfaces.

EXAMPLE 2

Preparation of Copolymers of Methyl Acrylate and N-Isopropyl Acrylamide

Copolymers of Methyl acrylate (MA) and N-Isopropyl Acrylamide (NIPAM) were made by polymerization in aqueous solution (or emulsion) at room temperature (25° C.) in five 20 mL screw-capped Pyrex vials. NIPAM (from Eastman) and MA (from BDH) were added to the vials containing 10 mL of water containing 2 mg sodium laurate in the weight ratio shown in Table 1. Each vial was then flushed with argon followed by the addition of 5 mg ammonium persulfate (from Aldrich) and 5 mg sodium bisulfite (from Aldrich) in aqueous solution (using 10 mL of water). After further flushing with argon, each vial was closed and allowed to stand overnight (14 h) at 25° C.

Evidence for complete polymerization was the complete absence of odor (MA) in all the vials and a flocculent emulsion in the two vials with the highest amount of MA. When warmed above room temperature, all the vials showed the presence of flocculated emulsion particles, which re-dissolved when cooled to −10° C.

As the temperature was raised, the copolymers precipitated again over a range of temperatures, as shown in Table I.

TABLE I

| | | Copolymers of MA and NIPAM | | |
|---|---|---|---|---|
| % MA | % NIPAM | Cloud Point (° C.) (↑) | Exotherm begins (° C.) (↓) | Exotherm Ends (° C.) |
| 0 | 100 | 21 | 32 | 20 |
| 20 | 80 | 17 | 26 | 2 |
| 30 | 70 | 14 | 25 | 15 |
| 40 | 60 | 0 | NA | NA |
| 50 | 50 | <−5 | NA | NA |

Referring to Table 1, the percent of MA with respect to the percent of NIPAM is shown. Also shown is the rising temperature (° C.) at which precipitation was first observed, which is listed as the "cloud point". Small (1 mg) samples of the solutions were also studied by differential scanning calorimetry (DSC) to determine the ambient temperatures, which are also shown, at which the exotherm began and ended, respectively.

Figure 2:
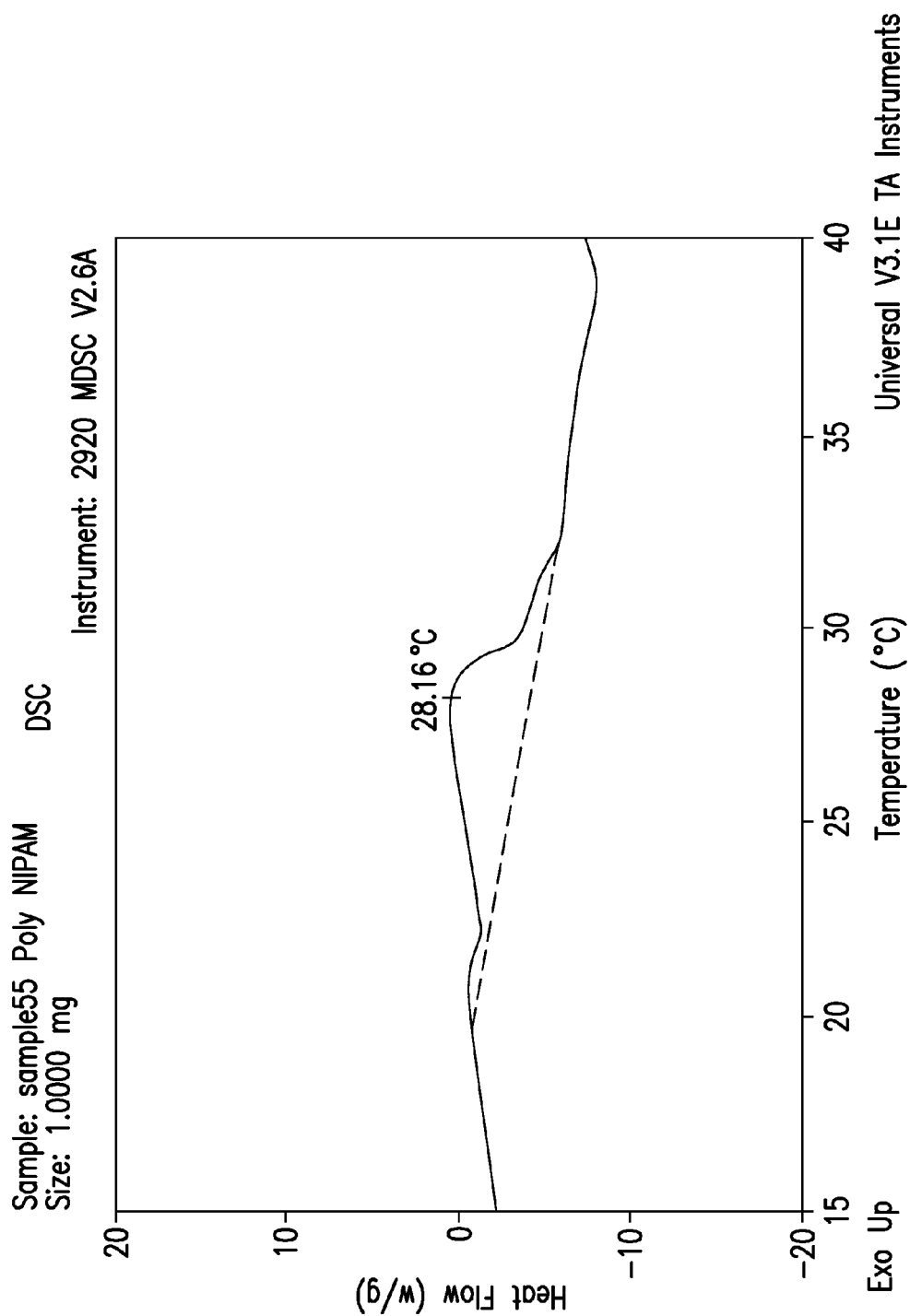
FIG. 2 is a DSC plot of heat flow versus temperature for NIPAM.
Figure 3:
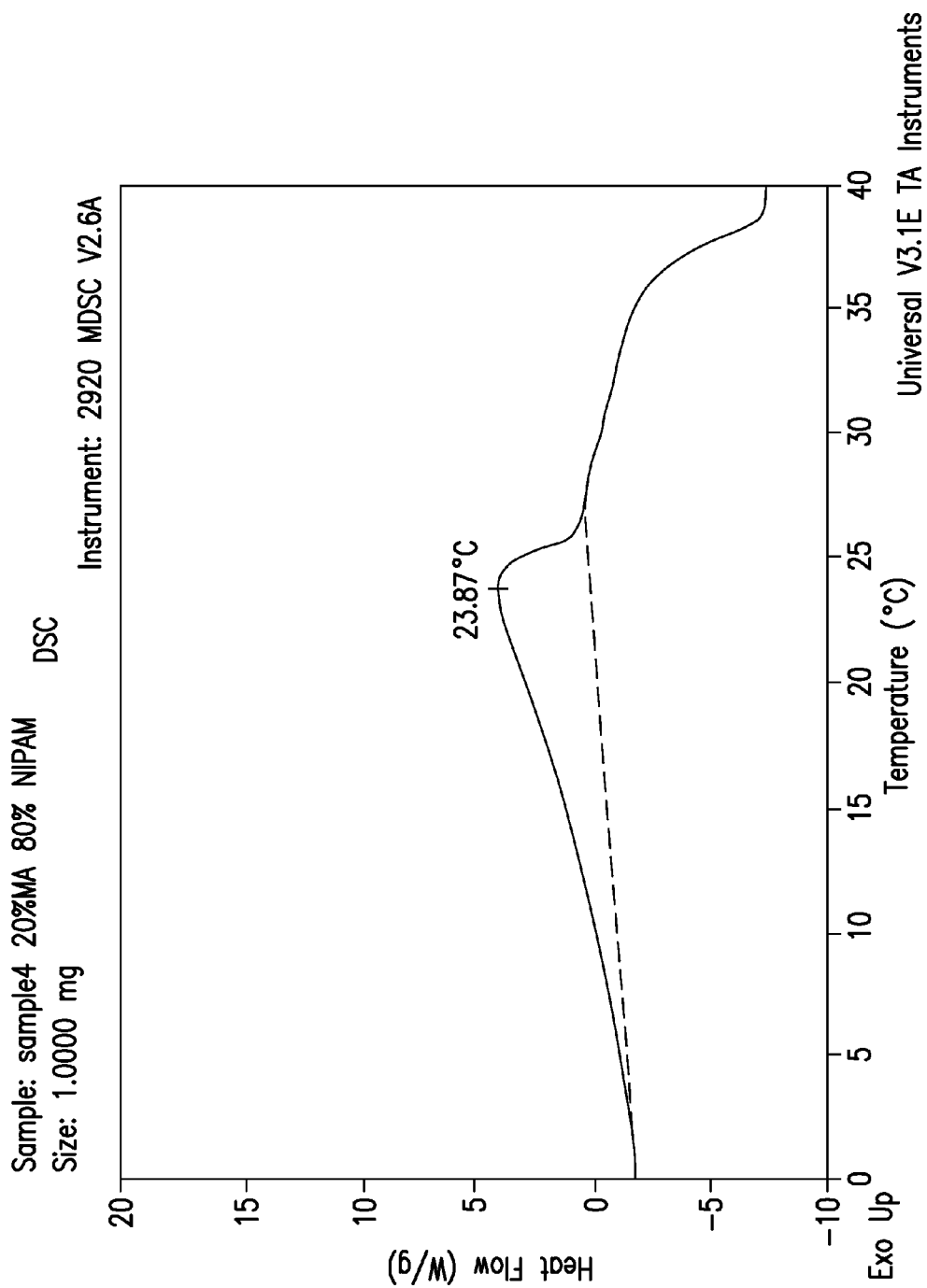
FIG. 3 is a DSC plot of heat flow versus temperature for 20 percent MA and 80 percent NIPAM.
Figure 4:
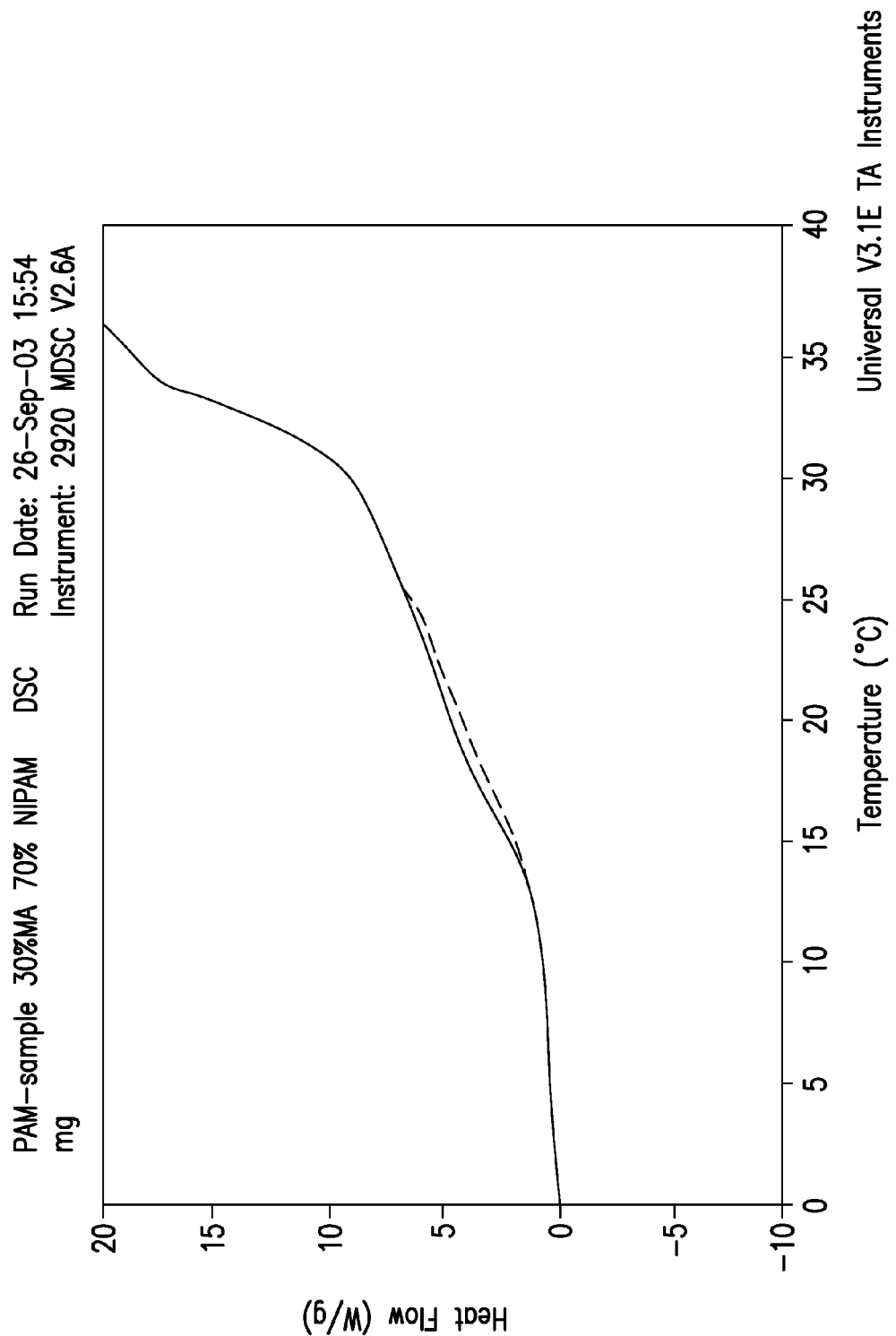
FIG. 4 is a DSC plot of heat flow versus temperature for 30 percent MA and 70 percent NIPAM.

FIG. 2 is a plot, obtained from a DSC device, of heat flow versus temperature for NIPAM. FIG. 3 is a plot, obtained from a DSC device, of heat flow versus temperature for 20 percent MA and 80 percent NIPAM. FIG. 4 is a plot, obtained from a DSC device, of heat flow versus temperature for 30 percent MA and 70 percent NIPAM. Both FIGS. 2 and 3 show exotherms starting at 31° C. and 27° C., respectively, and terminating close to 0° C., but the polymers in FIG. 4 showed no exotherm at any temperature.

The method of polymerization used in this example would lead to a relatively large range of copolymer compositions in each sample. However, using the polymerization method described in Example 1 should give narrower distributions, closer to 0° C. and hence be more useful in this application.

Figure 5:
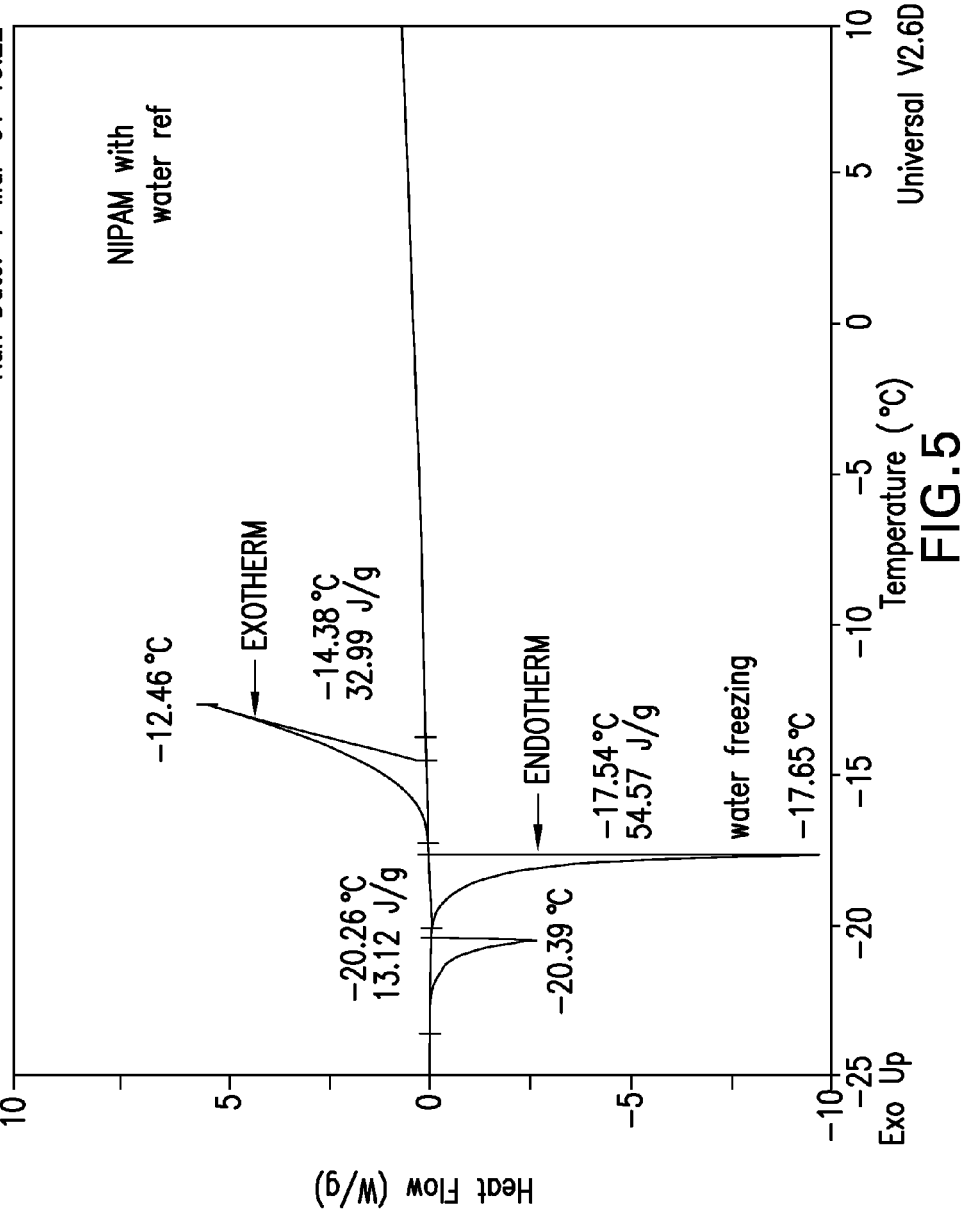
FIG. 5 is a DSC plot of heat flow versus temperature for 23 percent acrylonitrile and 77 percent NIPAM.

Copolymerizing different monomers with NIPAM can substantially move the exotherm range and substantially drop the peak exoterm temperature. For example, in a similar experiment, but using different monomers, i.e., 23 percent by weight acrylonitrile with 77 percent NIPAM in water, yielded an exotherm at much lower temperature (about −12.5° C.) and over a much narrower temperature range (from about −14° C. to about −17.5° C.). FIG. 5 is a plot, obtained from a DSC device, of heat flow versus temperature for 23 percent acrylonitrile and 77 percent NIPAM.

From these data, one can conclude (a) that copolymerization of hydrophilic monomers, such as for example, NIPAM, acrylic acid, methacrylamide, and/or acrylamide, etc., with hydrophobic monomers, such as for example MA, ethyl acrylate, butyl acrylate, and/or acrylonitrile, etc., can provide a precipitation temperature in the vicinity of 0° C. and (b) that such polymers could be useful in formulating sprays to protect sensitive plants from frost.

Moreover, additional polymers could also be used. For example, the polymer could be homopolymer formed from a single monomer (e.g., vinyl-methyl alcohol) having a hydrophobic substituent (e.g., the methyl) and a hydrophilic substituent (e.g., the alcohol).

Figure 6:
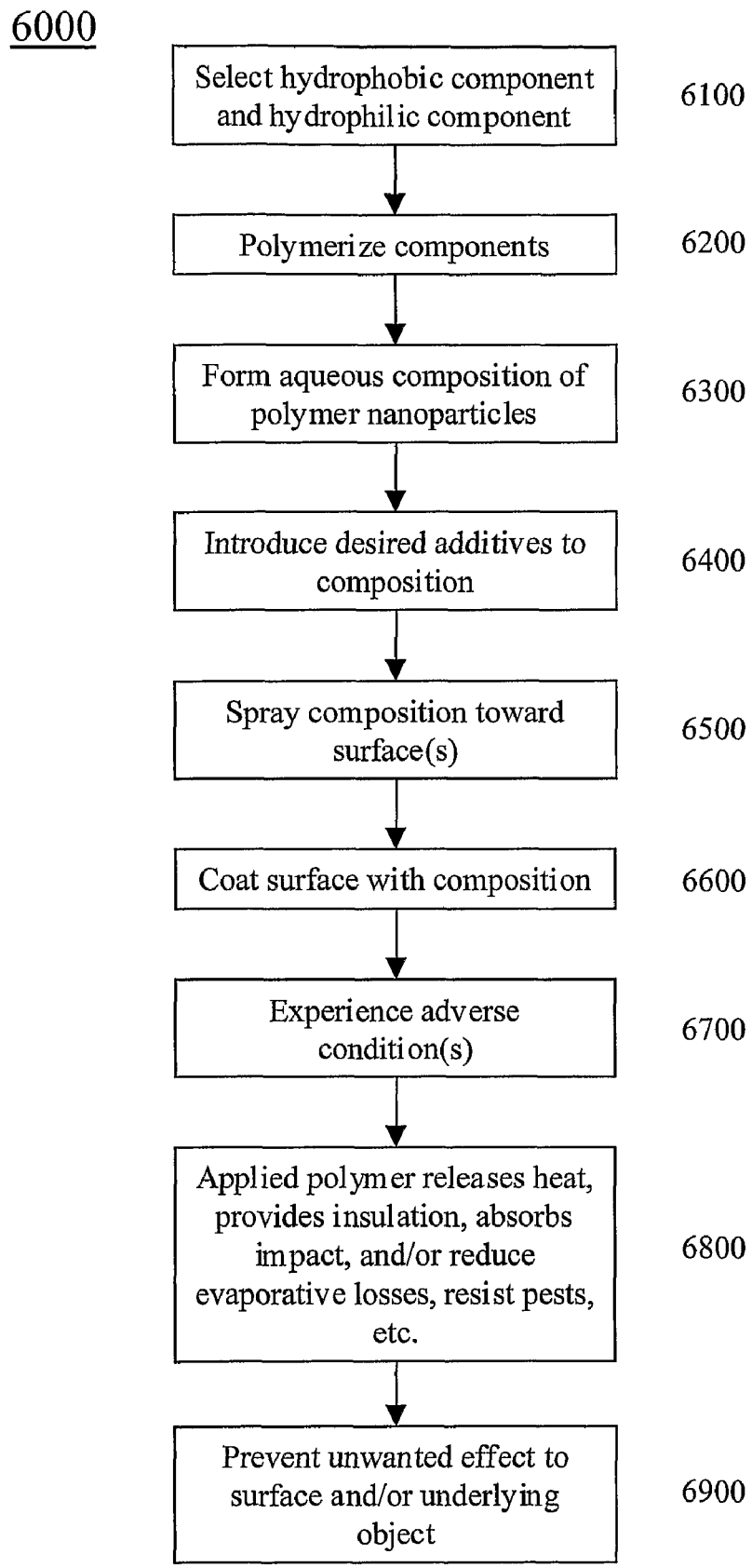
FIG. 6 is a simplified flow diagram for an exemplary method 6000.
Figure 8:
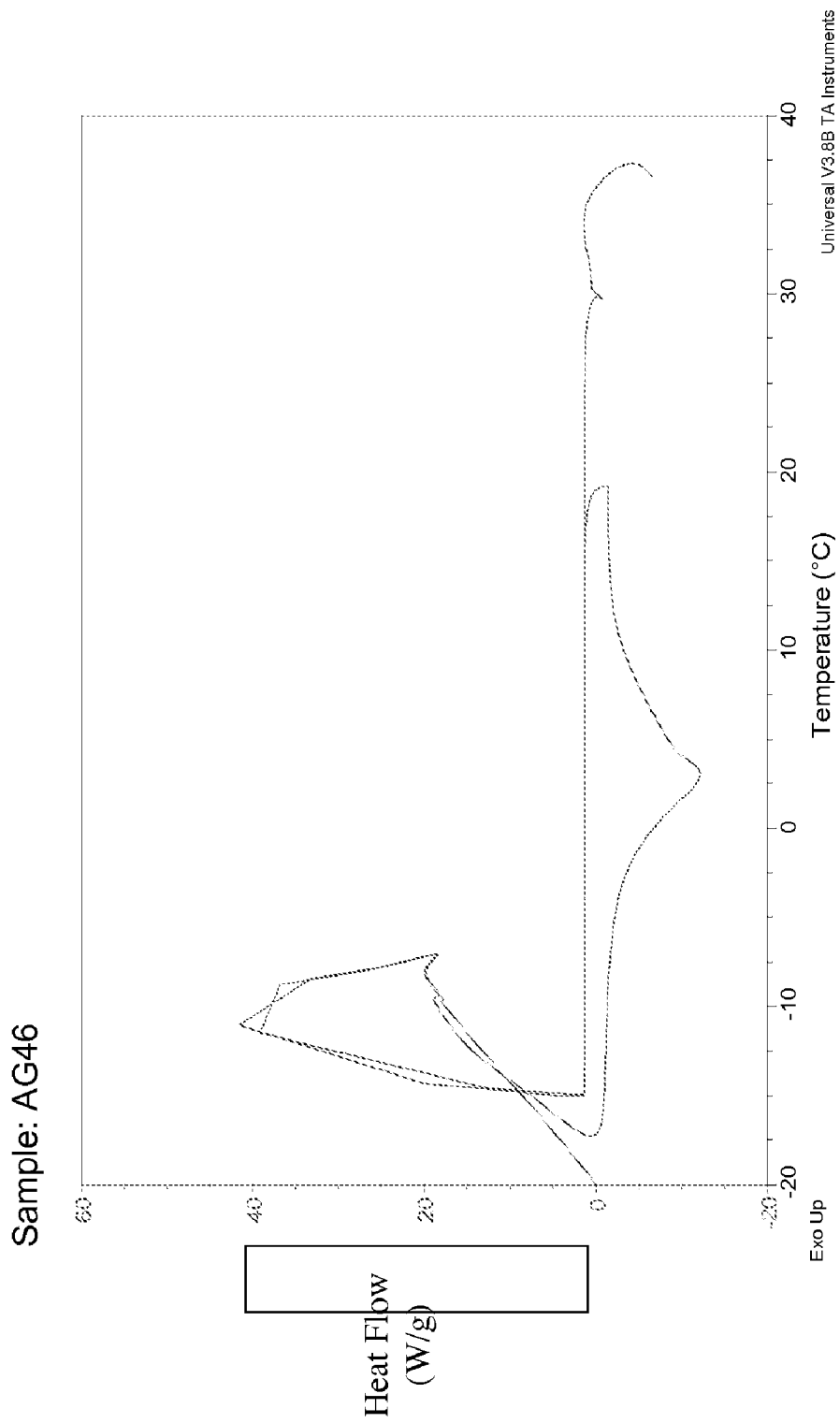
FIG. 8 is a DSC output for a hydrated sample of AG-46.
Figure 9:
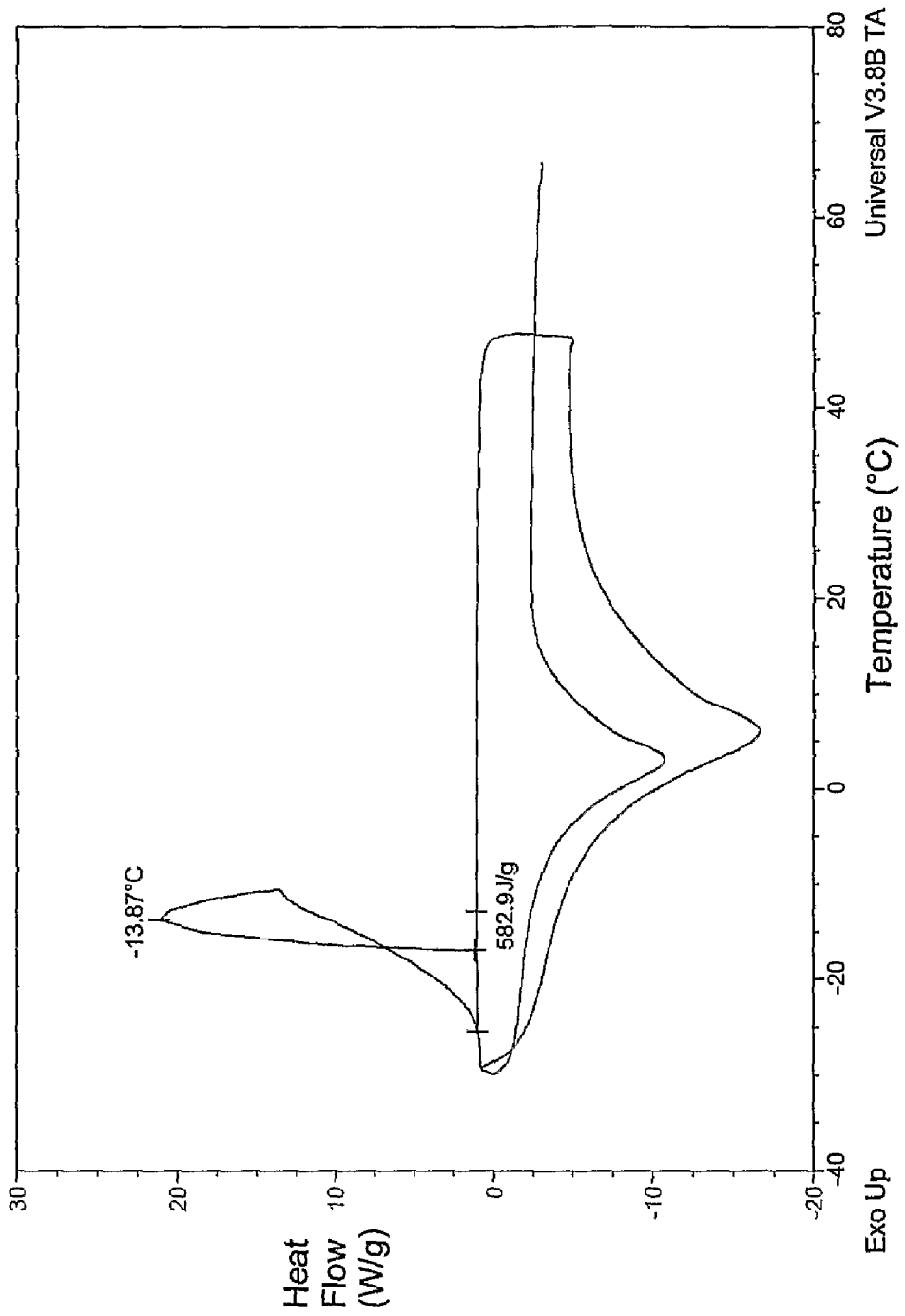
FIG. 9 is a DSC output for a hydrated sample of AG-46A.
Figure 10:
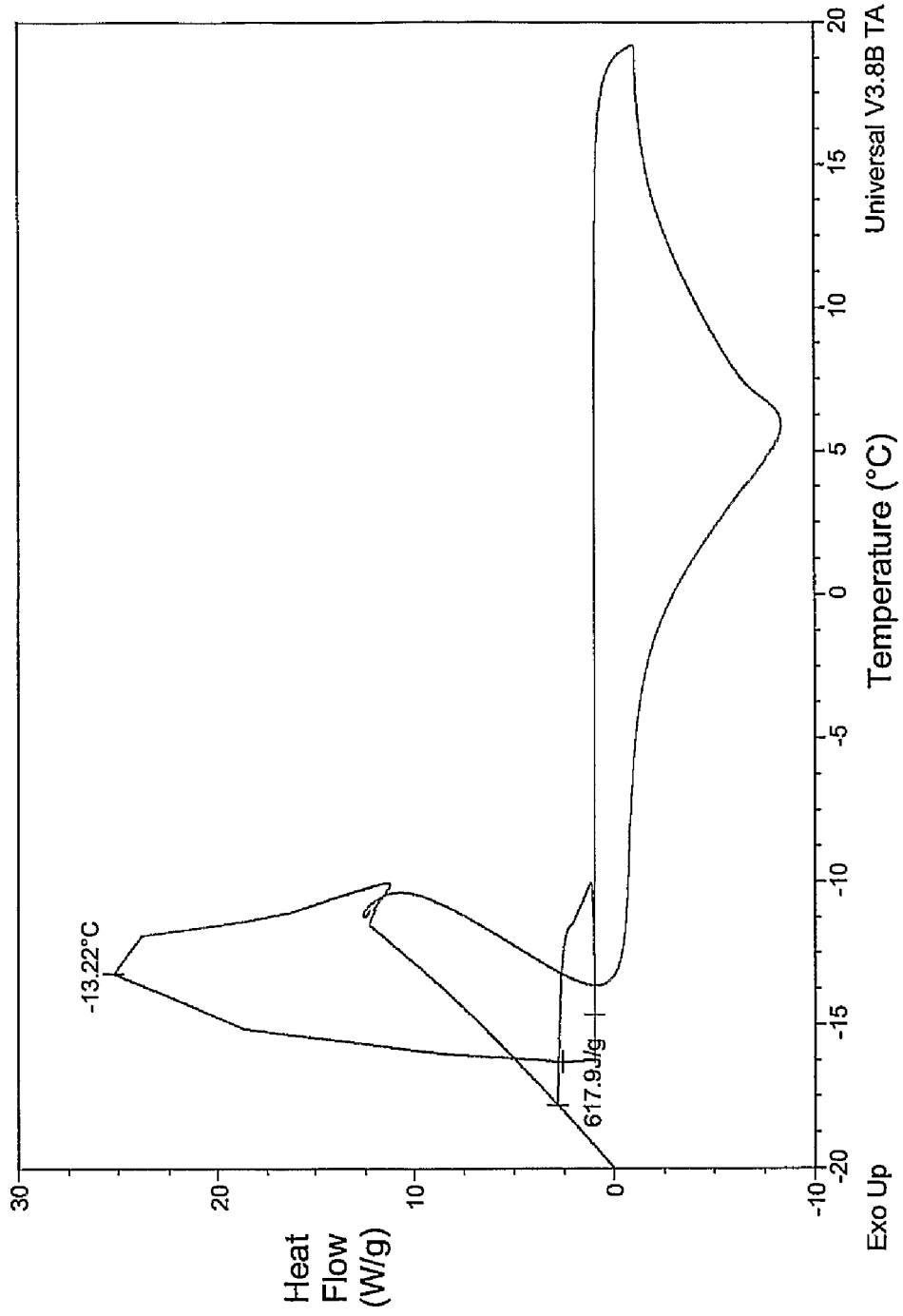
FIG. 10 is a DSC output for a hydrated sample of AG-47B.
Figure 11:
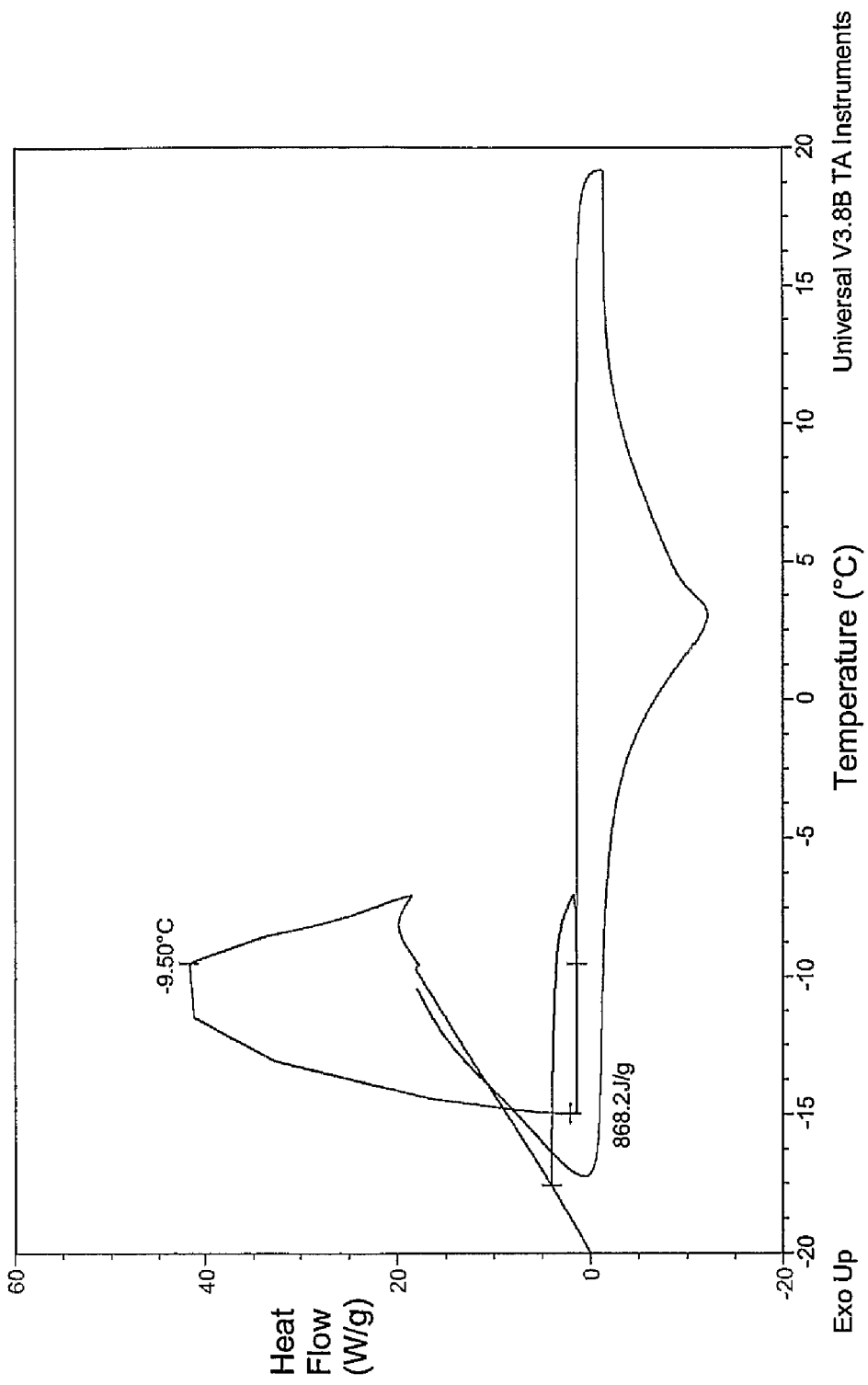
FIG. 11 is a DSC output for a hydrated sample of AG-50.
Figure 12:
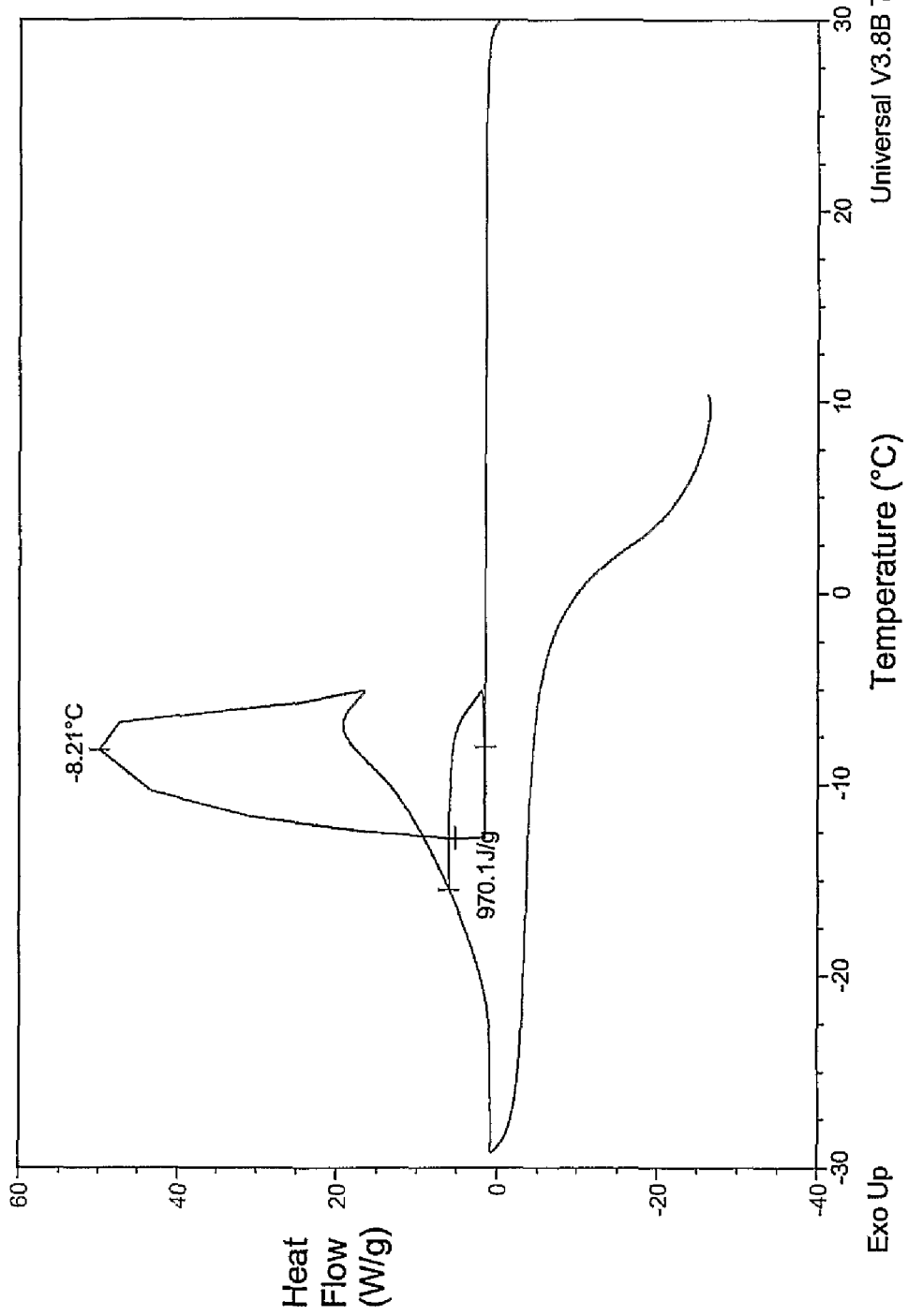
FIG. 12 is a DSC output for a hydrated sample of AG-14R.

FIG. 6 is a simplified flow diagram for an exemplary method 6000. At activity 6100, a hydrophobic material can be selected and a hydrophilic material can be selected. At activity 6200, the selected materials can be polymerized, copolymerized, and/or at least partially cross-linked. At activity 6300, an aqueous composition of polymer particles and/or nanoparticles can be formed. This composition can be a mixture, solution, dispersion, suspension, foam, and/or gel, etc.

At activity 6400, desired additives can be introduced to the aqueous composition, including for example, one or more micronutrients, macronutrients, pesticides, insecticides, herbicides, rodenticides, fungicides, biocides, plant growth regulators, fertilizers, microbes, soil additives, adhesion promoting-agents, surfactants, freezing point modifiers, heat releasing substances, hydrated polymer gels, foams comprising a hydrated polymer gel, and/or hydrated polymer gels comprising any of a hydrolyzed polyacrylonitrile, an uncrosslinked hydrolyzed polyacrylonitrile, a hydrolyzed fibrous protein, a hydrolyzed fibrous protein comprising amino acid and acrylamide moieties, and/or a hydrolyzed fibrous protein selected from hydrolyzed fibronectin, hydrolyzed fibrin, and hydrolyzed elastin, etc. Alternatively, the additives can be applied to the plant before, during, and/or after application of the composition.

At activity 6500, the composition (and/or additives, if applied separately from the solution) can be sprayed or otherwise directed toward one or more desired surfaces, such as a portion of a plant, aircraft, roadway, walkway, skin, etc. The composition (and/or additives) can include water droplets comprising a suspension and/or dispersion of polymer particles and/or water droplets coated with a polymer, such as a hydrated polymer gel. The composition (and/or additives) can be provided as a foam having air bubbles having a diameter in the range of from about 10 microns to about 100 microns. At activity 6600, at least a portion of a surface can be coated by the composition (and/or additives). After application, the composition (and/or additives) can dry, cure, harden, solidify, become more viscous, foam, polymerize, etc.

At activity 6700, the applied materials (e.g., composition, mixture, polymer, additives, etc.) can experience adverse conditions, such as dropping ambient temperatures, rising ambient temperatures, frost, freeze, dew, drought, low humidity, high humidity, and/or high temperatures, etc. At activity 6800, the composition, polymer particles, and/or applied materials can release heat, prevent ice formation, provide insulation, provide impact protection, reduce evaporative losses, allow transpiration, restrict transpiration, restrict mass transfer, and/or block and/or resist and/or repel diseases and/or pests, etc., to and/or from the coated surfaces. Thus, the applied materials can protect the coated surface and/or a portion thereof, from ice formation and/or from damage due to frost, freeze, drying, wilting, transport, impact, bruising, abrasion, vibration, premature ripening, rot, disease, and/or pests, etc.

This application incorporates by reference herein in its entirety, U.S. application Ser. No. 10/275,978, titled "Crosslinked Polymeric Nanoparticles and Metal Nanoparticles Derived Therefrom", filed May 23, 2003.

Additional approaches are possible. For example, a composition can be prepared from a Class 1 member, a Class 2 member, and a Class 3 member, said Class 1 member contributing approximately 0.1 percent to approximately 10 percent by dry weight of said composition, said Class 2 member contributing approximately 1 percent to approximately 10 percent by dry weight of said composition, and said Class 3 member contributing an amount up to a balance by dry weight of said composition. The composition can be a crosslinked hydrophilic acrylate elastomer.

The composition can be combined with water to form a mixture. At least a portion of a surface can be coated with the mixture. For example, at least a portion of a surface of a plant material can be coated with the mixture. As another example, the mixture can be applied to a surface to melt ice, and/or to retard and/or prevent the formation of ice.

The following examples describe some possible materials for the mixture, the composition, additives, and/or members of Classes 1, 2, and/or 3.

EXAMPLE 3

Select one or more monomers from Class 3, for example:
C1=Polypropylene glycol monomethacrylate
C2=Acrylic Acid
C3=Polyethylene glycol (400) monomethacrylate Add an acrylic terminated photo-initiator (D1) as a co-monomer at approximately 1 to approximately 3 percent dry weight level. D1 can be an oil soluable initiator such as $C_6H_5COC_6H_4(p-CH_2NMe_2Cl—CH_2CH_2OCOCHCH_2)$, "Quantacure" and/or $C_6H_5COC_6H_4(p-(OCH_2CH_2)_4OCO-CHCH_2)$, "Uvecryl", and/or a water soluble initiator such as ammonium persulfate (APS) and/or potassium persulfate, etc.

The composition of the monomer can be a blend of C1, C2 and C3, and D1, such that C1, C2 and C3 are in the range of approximately 0 to approximately 99.8 percent by dry weight, such as approximately 0 to approximately 50 percent by weight. D1 can be in the range of approximately 0.2 to approximately 5 percent by weight, such as approximately 1 to approximately 3 percent.

An alternative set of compositions can include one of the three choices, C1, C2, and C3 to be in the range approximately 93 to approximately 99.8 percent by dry weight.

Add a polymerization initiator from Class 2, such as a thermal free radical polymerization initiator (B1), such as acetyl peroxide, azobisisobutyronitrile, benzoyl peroxide, or cumene hydroperoxide at a weight level of approximately 0.1 to approximately 5 percent by dry weight of the monomer mix above, such as approximately 0.5 to approximately 3 percent, etc.

The mixture can be bulk polymerized (for hydrophilic monomer mixtures) or polymerized in an aqueous medium (suspension polymerization for a mixture of monomers containing at least one hydrophobic monomer). The typical process can involve placing the reactants in a flask, deaerating the reactants by bubbling through them a stream of dry nitrogen or other inert gas, or subjecting them to repeated freeze-pump-thaw cycles. The deaerated mixture then can be subjected to elevated temperatures (ranging from just above room temperature of approximately 25° C. to approximately 90° C.). In certain exemplary embodiments, the reactants can be subjected to a slow temperature ramp ranging from approximately 0.1° C. to approximately 5° C. per hour, gently stirring the mixture continuously, so that the reaction temperature rises from room temperature to an elevated state (approximately 30° C. to approximately 45° C.) over a period of several hours, then holding the temperature at that level for several hours, then resuming the temperature ramp until a further higher temperature is reached (approximately 40° C. to approximately 90° C., such as approximately 50° C. to approximately 75° C.) over several hours. The temperature is held at this level for an extended period of time, up to several hours.

In certain exemplary embodiments, the reactions can be performed at approximately 60° C. to approximately 90° C. In certain exemplary embodiments employing water-soluble and/or oil-soluble initiators, redox initiators can be utilized for polymerizations at approximately 60° C. to approximately 70° C. In certain exemplary embodiments employing suspension/solution polymerization, water can be taken in the kettle and reactants with water can be added over time. Temperature can be ramped up in bulk polymerizations where reactants are taken into kettle before the reaction.

The total time of polymerization can range from approximately 2 to approximately 24 hours, such as approximately 4 to approximately 10 hours. A polymer produced as above can have a molecular weight in the range approximately 20,000 to approximately 1,000,000. The molecular weight distribution (Mw/Mn) can be in the range approximately 1.0 to approximately 5.0, such as approximately 1.0 to approximately 2.0, and/or approximately 1.0 to approximately 1.50.

According to Mattiel, et al., Macromol. Theory Simul., 1996, 6, 499-523, the behavior of polymers in solvents can depend on the nature of the interaction between the solvent molecules and the polymer molecules. Therefore, when a polymer is brought into physical contact with plenty of solvent, three scenarios can result.

a) The solvent molecules and polymer chains have high affinity for each other. The polymer chains therefore expand, preferring to interact with the solvent molecules rather than their own. Such solvents are termed good solvents for the polymer.
b) The solvent molecules and polymer chains have very little affinity for each other. The polymer chains therefore clump into a ball as they prefer to interact with themselves rather than the solvent molecules. Such solvents are termed poor solvents for the polymer.
c) Theta solvents mark the boundary between good solvents and poor solvents. In this case, the interaction between the polymer chains themselves and between the polymer chains and solvent molecules are equal. The polymer forms a random coil in such solvents.

Thus, a suspension of a polymer of interest can be formed in a mixture of water and/or a water-miscible non-solvent, e.g., tetrahydrofuran, isopropyl alcohol, and/or cyclohexanol, such as a suspension formed by dissolving the polymer in water, and adding a non-solvent so as to approach the composition of a theta solvent.

A mixture of said suspension and one or more multifunctional monomers belonging to Class 1 can be formed by adding multifunctional monomers to the suspension formed as above. Examples of these multifunctional monomers include:

Propoxylated neopentyl glycol diacrylate (commercially available from Sartomer corporation under the tradename SR 9003) (A1)
Ethoxylated trimethylol propane triacrylate (A2)
Alkoxylated diacrylate (A3)
Pentaerythritol triacrylate (A4)

The total weight of the added multifunctional monomer can be in the range approximately 0.1 to approximately 10 percent by dry weight of the polymer, such as approximately 1 to approximately 8 percent, and/or approximately 2 to approximately 6 percent, etc.

The relative amount of each of the choices can be as follows: (A1, A2, A3) in the range approximately 0 to approximately 100 percent by dry weight of the added monomers; A4 in the range approximately 0 to approximately 50 percent by dry weight of the added monomers.

This mixture and/or suspension then can be irradiated with UV radiation to cross-link the polymer through copolymerization of the added multifunctional monomers. Upon completion of reaction, the resulting mixture and/or suspension then can be centrifuged to separate from the liquid medium, washed free of unreacted monomers, then freeze dried.

A dry powdery polymer can formed by separating the suspension by freeze drying upon completion of the cross linking process. This powder then can be re-mixed and/or re-suspended in water (dry weight of polymer being in the range approximately 0.1 to approximately 10 weight percent, such as approximately 0.5 to approximately 5 percent, etc.).

In a series of experiments, a number of exemplary polymers were synthesized. These polymers were designated AG 46, AG 46A, AG 47B, AG 50, and AG 14R.

EXAMPLE 4

Synthesis of AG 46

This example illustrates the synthesis of a polymer containing and/or formed from internally plasticizing, long-chain hydrophilic monomers. Three steps were utilized prior to the polymer synthesis.

A 1 L reactor kettle equipped with a stainless steel impeller and fitted with a condenser was charged with 100 grams of deionized (DI) water and placed in a water bath at 70° C. (with slow nitrogen purging).

Afterwards, 50 grams of DI water was weighed in a 250 mL glass beaker. Next, 25 grams of ethoxylated (5) hydroxyethyl methacrylate (namely, CD-571 available from Sartomer of Exton, Pa.), 5 grams of acrylamide (commercially available from Acros), 3 grams of acrylic acid (commercially available from Aldrich), 2 grams of ammonium persulfate (APS) (commercially available from Aldrich) and 2 grams of polypropylene glycol diacrylate (commercially available from Acros) were weighed and charged to the beaker in that order. The mixture was gently stirred with a magnetic stirrer for 10 minutes.

Two chaser solutions were prepared as follows: a) 0.2 grams of APS and 0.33 grams of tert-butyl hydroperoxide (70 percent solution) (commercially available from Aldrich) dissolved in 3 mL of water, and b) 0.25 grams of sodium metabisulfite solution (commercially available from Acros) dissolved in 3 mL of water.

The monomer mixture was added to the 1 L reactor kettle over one hour at a constant rate using the Camile® Data Acquisition and Control system, available from Sagian, Inc. of Indianapolis, Ind. The stirring was gradually increased from 80 rpm to 330 rpm to ensure proper mixing. 15 minutes after the monomer addition was complete, the two chaser solutions were fed to the kettle over one hour via a syringe pump.

The polymer was diluted further with DI water. The polymer solution exhibited the following properties: particle size 140 nanometers; minimum filming temperature (MFT) <0° C.; solid content 12.8 percent.

EXAMPLES 5, 6, AND 7

AG 46A, AG 47B, AG 50

The polymers AG 46A, AG 47B, and AG 50 were synthesized following the same procedure as described in Example 4 above. The materials used to synthesize the polymer samples are given in Table II.

TABLE II

| | Polymer Ingredients | | |
|---|---|---|---|
| Ingredients (grams) | AG 46 A | AG 47 B | AG 50 |
| DI Water | 130 | 150 | 200 |
| Sodium bicarbonate | 2 | 0 | 0 |

TABLE II-continued

| | Polymer Ingredients | | |
|---|---|---|---|
| Ingredients (grams) | AG 46 A | AG 47 B | AG 50 |
| Sartomer CD 571 | 25 | 25 | 30 |
| Acrylamide | 5 | 0 | 0 |
| N-isopropyl acrylamide | 0 | 5 | 5 |
| Acrylic acid | 3 | 3 | 5 |
| APS | 2 | 2 | 2 |
| PPG diacrylate | 2 | 2 | 3 |

The amounts of DI water in step 2 (as in Example 4) were 30 grams, 50 grams and 100 grams for AG 46A, AG 47B and AG 50, respectively. All the polymers had MFT <0° C., and residual monomer <0.5 percent as determined by gas chromatography.

EXAMPLE 8—AG 14R

This example also illustrates the synthesis of a polymer containing and/or formed from internally plasticizing, long-chain hydrophilic monomers. Three steps were implemented prior to the polymer synthesis.

A 1 liter reactor kettle equipped with a stainless steel impeller and fitted with condenser was charged with 100 grams of DI water and placed in a water bath at 70° C. (with slow nitrogen purging).

Approximately 80 grams of DI water was weighed in a 250 mL glass beaker. Next, 3 grams of polyoxyethylene sorbitan monooleate (also known as Polysorbate 80 or Tween® 80, available from ICI Americas of Bridgewater, N.J.), and 1.65 grams of sodium bicarbonate (commercially available from Aldrich) were added to the beaker. The mixture was gently stirred with a magnetic stirrer at ambient conditions for 15 minutes. Next, 20 grams of CD 571, 7 grams of acrylamide (commercially available from Acros), 2 grams of acrylic acid (commercially available from Aldrich), 10 grams of TRG1, 2 grams of APS (commercially available from Aldrich), and 1 grams of polypropylene glycol diacrylate (commercially available from Acros) were weighed and charged to the beaker in that order. The mixture was stirred at 1800 rpm for 10 minutes to prepare the pre-emulsion.

Two chaser solutions were prepared as follows: a) 0.2 grams of APS (commercially available from Aldrich) and 0.33 grams of tert-butyl hydroperoxide (70 percent solution) (commercially available from Aldrich) dissolved in 3 mL of water, and b) 0.25 grams of sodium metabisulfite solution (commercially available from Acros) dissolved in 3 mL of water.

The pre-emulsion was added to the 1 L reactor kettle over one hour at a constant rate using the Camile® system while maintaining the temperature of water bath at 70° C. The stirring was gradually increased from 80 rpm to 330 rpm to ensure proper mixing. Approximately 15 minutes after the pre-emulsion was complete, the two chaser solutions were fed to the kettle over one hour via a syringe pump. The polymers had MFT <0° C., and residual monomer <0.5 percent as determined by gas chromatography.

Polymer Composition

FIG. 7 lists the composition by weight, percentage by weight (water included), and relative percent composition (water excluded), respectively, for each of polymers AG 46, AG 46A, AG 47B, AG 50, and AG 14R.

Preparation of TRG1

The TRG1 monomer used for certain exemplary polymers is a methacrylated derivative of linoleic acid, and thus a member of Class 3. The ingredients for TRG1 are as follows:

| | |
|---|---|
| Sartomer CD-571 | 287.20 grams |
| Pamolyn 240 (Eastman) | 212.70 grams |
| Toluene (Aldrich) | 400.00 grams |
| Phenothiazine (Aldrich) | 0.24 grams |
| Hydroquinone (Aldrich) | 0.24 grams |
| p-Toluene sulfonic acid (Aldrich) | 5.00 grams |

The reaction apparatus for preparing TRG1 is as follows:
3-neck 1000 mL round bottom flask
Center neck—Glass stir rod with bearing
Side neck #1—Dean-Stark trap with condenser
Side neck #2—Nitrogen inlet
The reaction procedure for preparing TRG1 is as follows:
a. Weigh all reactants into flask and purge for five minutes with nitrogen.
b. Mount the flask into a heated water bath (100° C.±10° C.).
c. Fill the Dean-Stark trap with toluene and continue the reaction for approximately 3 hours.
d. Keep nitrogen purging throughout the reaction to ensure water removal.

Preparation of TRG2

The TRG2 composition used for certain exemplary polymers is a soybean protein composition. To prepare TRG2, a 2 L reaction kettle was charged with 1359.2 grams of water, 5.2 grams of zinc sulfate heptahydrate (commercially available from Acros), 34.2 grams of calcium oxide (commercially available from Fisher), and 34.2 grams of sodium benzoate (commercially available from Aldrich). The reaction kettle lid was fitted with a four-propeller stirrer, rubber septum, and clamp. The lid was then securely attached to the kettle and the kettle was submerged in a water bath heated to 50° C. The stirrer was attached to a mechanical stirring motor and the contents of the kettle were stirred for five minutes at 600 rpm. Approximately 400 grams of soy protein isolate (commercially available as PRO-FAM(R) 974 from Archer Daniels Midland Company, Decatur, Ill.) were added over the course of 20 minutes. The mixture was allowed to homogenize for approximately 30 minutes and 110.2 additional grams of soy protein isolate were added.

The mixture was reacted for an additional 60 minutes at 1200 rpm. Next, 105.4 grams of wax emulsion (commercially available as Cascowax EW from Borden Chemicals) were added and allowed to homogenize with the reaction mixture for 15 minutes. Upon complete incorporation of the wax emulsion, the adhesive was removed from the water bath. The resulting adhesive had a solid content of 30 percent.

Polymer Samples

Using the exemplary polymers described above, certain samples were prepared and tested. These samples were labeled TRG 308-9, TRG 308-10, TRG 308-11, TRG 308-12, and TRG 308-13. Each sample was tested and found not to be phytotoxic.

Preparation of TRG 308-9

A polymer solution of AG 46 was designated as TRG 308-9. The polymer solution of AG 46, having a solids content of approximately 21 percent by dry weight, was diluted further with DI water to reduce viscosity and the solids content was adjusted to approximately 12.8 percent by dry weight.

Preparation of TRG 308-10

TRG 308-10 was obtained by diluting polymer AG 46A, having a solids content of approximately 23 percent by dry weight, with DI water to a solids content of approximately 21 percent by dry weight.

Preparation of TRG 308-11

To prepare TRG 308-11, in a 2 L glass kettle (fitted with water condenser, stainless steel and a stoppered outlet for addition), 105 grams of Pro-Cote® 5000S (a hydrophically-modified soybean protein commercially available from Dupont Soy Polymers) was dissolved in 500 grams of DI water, under stirring at 70° C. After stirring for 45 minutes, the temperature was lowered to 40° C. and 200 grams each of AG 14R and AG 50 was added in to it. The mixture was stirred at 400 rpm for 30 minutes to prepare the dispersion. The final solids were adjusted to approximately 16.2 percent by dry weight by adding DI water at 40° C.

Preparation of TRG 308-12

The TRG 308-12 sample was prepared by blending AG 47B and TRG2 in the ratio 40:60.

Preparation of TRG 308-13

The TRG 308-13 sample was prepared by dissolving commercial grade potassium salt of acrylic acid—co—acrylamide (obtained from Aldrich) in DI water. To that solution, 1 weight percent polypropylene glycol diacrylate, and 0.1 weight percent Irgacure 2959 (1-[4-(2-hydroxyethoxy)-phenyl]-2-hydroxy-2-methyl-1-propane-1-one photoinitiator, available from Ciba Specialty Chemicals Inc.) were added and the blend was irradiated with ultraviolet radiation for 30 minutes. The solids content of the resulting polymer was adjusted to 11 percent by dry weight with DI water.

Testing of Samples

Each of the samples (i.e., TRG 308-9, TRG 308-10, TRG 308-11, TRG 308-12, and TRG 308-13), contained less than 0.5 percent by dry weight of residual monomers (determined via gas chromatography).

Testing of Polymers

Polymer particle sizes were determined using a Microtrac UPA 250 Particle Size Analyzer and are listed in Table III.

TABLE III

| | Particle Size | |
|---|---|
| Polymer | Particle size in nanometers |
| AG 46 | 140 nm |
| AG 46A | 173 nm |
| AG 47B | 194 nm |
| AG 14R | 142.3 nm |
| AG 50 | 187 nm |

Certain exemplary polymers in a dry state can have glass transition temperature above approximately −50° C. and below approximately +50° C., and/or cross-link density range beginning at approximately 0.5 percent but not exceeding approximately 20 percent, such as approximately 5 to approximately 20 percent.

Certain exemplary polymers can be capable of interacting with water. Certain exemplary polymers, such as those in the form of hollow micelles, can be capable of enclosing water droplets. When formed as nanoparticles and/or solid nanoparticles, certain exemplary polymers are capable of being coated by water. Because these polymers can incorporate hydrophilic as well as hydrophobic segments, and/or between 1 and 11 hydroxyl groups, and since they can have the desired chain length and/or the desired range of cross links per mole, these products can be capable of developing attractive interaction with water through the formation of hydrogen bonds, and/or at the same time form water-rich domains inside the particle through dispersive interactions. The water molecules and bulk water associated with these products need not be primarily physically entrapped therein. The coexistence of different type of interactions between these particles and water can provide an inhomogeneous combination of bound water inside the particles and/or as a coating on them. The simultaneous presence of weakly and strongly bound (complexed) water can provide a freezing exotherm peak that is spread out over a broad temperature range.

The complex can demonstrate an exotherm reaction ranging from approximately 5° C. (or higher) to approximately −16° C. Although the precise nature of the exotherm is not necessarily clearly understood at this time, it is theorized that the peak of the exotherm can be shifted to any temperature selected from the normal freezing point of water (approximately 0° C.) to substantially below the normal freezing point of water (e.g., −16° C.), due to supercooling effects and/or inhibition of formation of ice microcrystals that can serve as nucleating agents of bulk freezing.

Supercooling effects are discussed by Janssen, A. H. et al. in "Homogeneous Nucleation of Water in Mesoporous Zeolite Cavities", Langmuir 2004, 20:41-45 and by Rosenfeld, Daniel, et al. in "Deep Convective Clouds with Sustained Supercooled Liquid Water Down To −37.5° C., Nature, Vol. 405, May 25, 2000, pages 440-442, both of which are incorporated by reference herein in their entirety.

The nature of the freezing process experienced by complexed or bound water can be measured by performing differential scanning calorimetry (DSC). FIGS. 8-12 are DSC thermograms for hydrated (e.g., 80 percent water, 20 percent dry weight polymer) samples of AG-46, AG-46A, AG-47B, AG-50, and AG-14R, respectively. FIGS. 8-12 shows that the exotherms for their respective polymers are spread approximately over the ambient temperature ranges listed in Table IV.

TABLE IV

Exotherm Temperature Ranges

| Polymer | Exotherm Temperature Range ° C. | |
|---|---|---|
| | Upper | Lower |
| AG 46 | −7 | −15 |
| AG 46A | −12 | −15 |
| AG 47B | −10 | −16 |
| AG 50 | −7 | −15 |
| AG 14R | −5 | −13 |

Note that polymers AG-47B and AG-50 are formed from NIPAM, and show exotherms spanning temperatures well below 0° C. Likewise, polymers formed from NIPAM have been shown herein to produce exotherms spanning temperatures well above 0° C. Thus, using the principles taught herein, one can design polymers that are formed from NIPAM and/or other Class 3 members, including polymers formed from approximately 0.5 percent or less by dry weight of a Class 1 member and/or approximately 10 percent or greater by dry weight of a Class 2 member, that will provide an exotherm over any predetermined and/or desired ambient temperature range within the range of approximately 30° C. to approximately −16° C.

The heat generated by the polymers of FIGS. 8-12 during their exotherms is shown in Table V.

TABLE V

Heat Generated during Exotherm

| Polymer | Heat Generated | |
|---|---|---|
| | J/g | Cal/g |
| AG 46 | ~540 | ~130 |
| AG 46A | 582.9 | 139.2 |
| AG 47B | 617.9 | 147.6 |
| AG 50 | 868.2 | 207.3 |
| AG 14R | 970.1 | 231.6 |

As shown in Table V, the exotherm for AG-46 produces a heat of approximately 130 calories per gram, well over the theoretical amount to be expected on the basis of water content (80 percent by weight of water would be expected to yield an exotherm of approximately 64 calories per gram).

For certain exemplary embodiments, the magnitude of the exothermic freezing process can be modeled by the following formula:

80×A (percent weight water comprises of the suspension)×B (a multiple of the latent heat of water between approximately 0.5 and approximately 2.5).

For example if the suspension is 10 percent by weight water then A is equal to 0.1 and B depends on the chemical structure of the frozen water-polymer complex, that is controlled by the chemical structure of the polymer, which in turn determines the strength of the complexation of water molecules with the polymer network. For example, in FIG. 8, A is 0.8, and B is 2.03.

Figure 13:
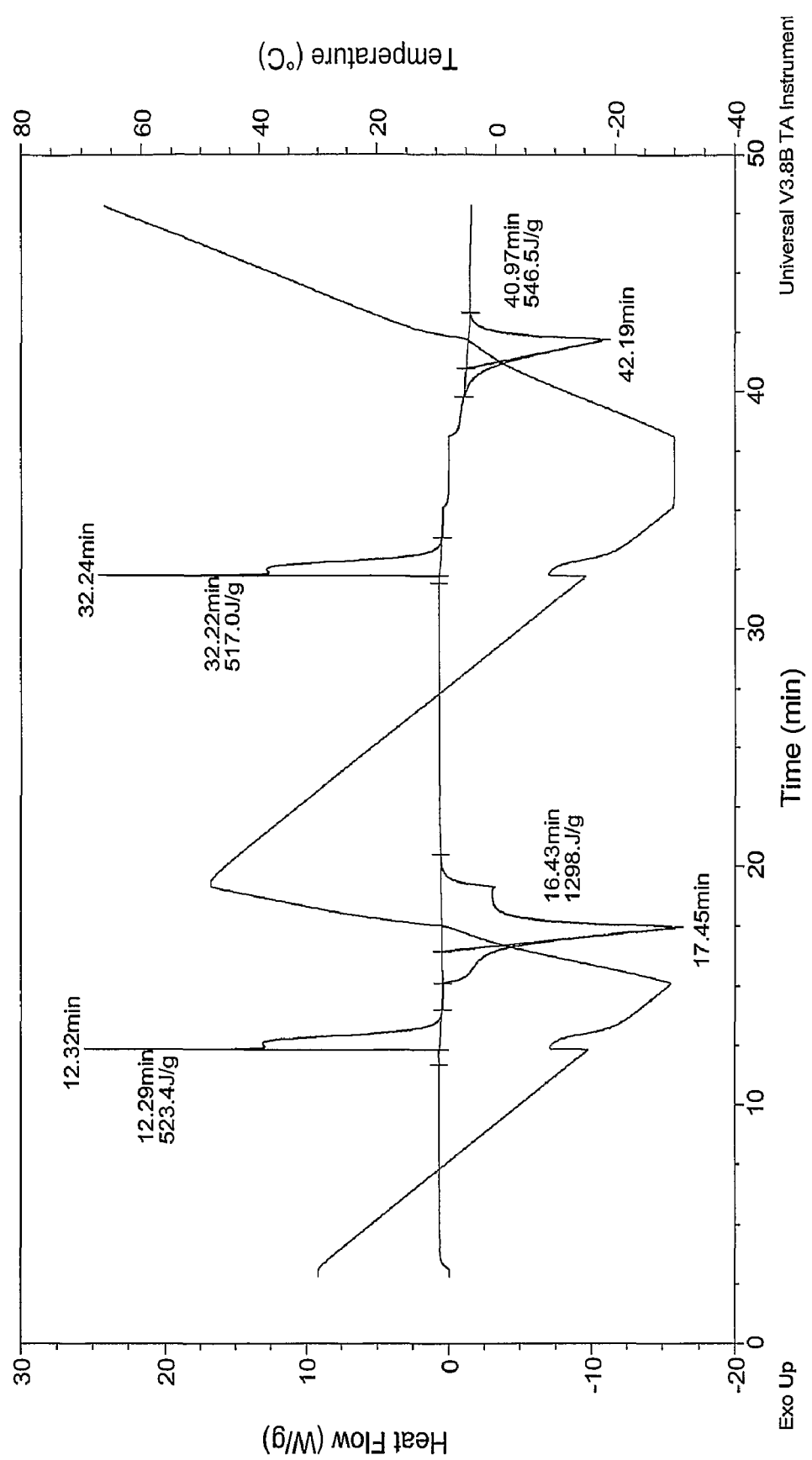
FIG. 13 is a DSC output for a hydrated sample of AG-47A.

FIG. 13 is a DSC output of an exemplary polymer (AG-47A, which is identical in composition to AG-47B) showing how the exothermic reaction is repeatable as ambient temperature varies through a range bounded by a temperature above the exotherm range and a temperature below the exotherm range. FIG. 13 also shows that the ability of the polymer to undergo the exotherm is "recharged" by a rise in ambient temperature above the range of the exotherm.

Freeze Protection

Differential scanning calorimetry can provide a quantitative measure of the freeze protection capability of the polymer and/or can be useful in determining the optimum amount of water that can be added to the dry polymer to develop a sprayable and/or coatable formulation. DSC studies can be performed on a number of suspensions and/or mixtures each containing a different amount of water to the dry weight of the polymer. As the percent composition of water increases, B can move closer to 1.0, indicating that the mixture behaves more and more like essentially pure water. Typically, the formulation can contain water in the range approximately 90 percent to approximately 99.5 percent of the weight of the suspension and/or mixture, such as approximately 92 percent to approximately 99 percent, the rest being dry polymer. As the per cent composition of water exceeds approximately 99 percent, the freezing peak can become sharper indicating that the exotherm is being confined over a narrower temperature range.

Dehydration

Certain exemplary polymer suspensions in water also can provide protection against dehydration (e.g., loss of water through evaporation), from plant materials, plants, flowers, skin, and/or surfaces, etc. In the case of plant materials, such dehydration can before and/or after being harvested. For example, left unprotected, harvested plant products can continue to lose water, unless they are maintained in a closed environment that is saturated with water vapor. Application of these polymer-water complexes as a protective layer can inhibit loss of water from the plant products. The complexed water can evaporate slowly, and/or the added layer can retains its protective function as long as the added layer retains water.

If applied prior to harvest, the protective layer can reduce irrigation requirements, excessive surface temperatures, etc. Use of a sticky substance, such as a "sticker", can assist the protective layer with adhering to the plant material. Application of water to a "dried" protective layer can potentially recharge the process, thereby providing additional protection against frost, freeze, temperature, radiation, transpiration, dehydration, heat transfer, mass transfer, kinetic energy, impact, diseases, and/or pests, etc.

Generally speaking, the loss of water from the protective layer is not necessarily uniform, since the layer can incorporate a mix of strongly and weakly bound water molecules including water that is physically entrapped. The water that is weakly bounds can leave first, and the rate of loss of water from the protective layer can slow down. Ultimately, as the layer approaches the composition of dry polymer, the polymer can become a recipient of water from the underlying plant tissue. The transfer of water from the plant products to the protective layer can be inhibited as long as there is any significant bound water left in the protective layer. Therefore, at least some portion of the incorporated water can be strongly complexed to the polymer so that its evaporation is strongly inhibited.

The heat of vaporization of pure water is approximately 9.7 kcals/mole, a quantity that will increase if the water being vaporized is complexed to a substrate. If the complex provides a stabilization of approximately 0.5 kcals/mole, well within the capability of complexes formed through the formation of hydrogen bonds between the water molecules and the hydroxyl groups incorporated in the polymeric network, then the rate of evaporation of water from the protective layer can be reduced by about a factor of approximately 100 at approximately 30° C., a typical storage and transporting temperature, relative to the rate of evaporation of pure water at the same temperature. For example, the vapor pressure of pure water is about 2.5 mm at 30° C., while the complexed water can have a vapor pressure of approximately 0.025 mm if complexation adds approximately 0.5 kcals/mole of stabilization, and thus can increase the heat of vaporization by an equivalent amount. In practice, the enthalpy of complexation need not be single quantity, but can vary from about 0.1 kcals/mole to about 2.0 kcals/mole. An additional characteristic of the protective layer can be that as it loses water it can continue to slow down the evaporation of the residual water, potentially leading to a prolonged increase in the total period of protection provided by this layer. Therefore, a range of inhibition of water loss from plant materials can range from a factor of approximately 2 to approximately 100 upon application of the protective layer.

Biodegradability

The protective layer can be composed of a complex of water and an aliphatic polymer that is highly crosslinked and that can contain residues of UV initiators. For example, phenyl end groups can serve as termination points of the network. Such a material can undergo relatively rapid photo-degradation in sunlight and/or can undergo photo-oxidative and/or photo-oxidative chain scission within a few days following application. This type of degradation typically causes the polymeric coating to become brittle and/or it can easily peel off from the plant organs and/or it can be leached out into the ground. The polymer can continue to oxidize and/or photo-degrade, ultimately forming soluble acids and alcohols that can be absorbed by the soil and will not be harmful to the plants. If the plant products protected by this material are picked before the layer has eroded away due to natural photo-degradation, the layer can continue to oxidize and/or photo-degrade after the plant products are harvested. The polymer has been tested to be non-toxic to plants and/or non-phytotoxic, and given the rapid potential rate of oxidation and/or photo-degradation, little of the polymer is expected to survive the storage and transportation process.

Wound Care

Certain exemplary embodiments can provide polymers, mixtures, and/or compositions suitable for wound healing applications. Such materials can demonstrate any of the following properties:

1. Biocompatibility.
2. Hydrophilicity, with water uptake in the range of approximately 20 percent to approximately 40 percent, such as from approximately 25 percent to approximately 35 percent by weight of dry material.
3. Cross-linked structure in order to ensure that the dressing remains intact for a predetermined period of time from approximately 1 day to approximately 1 week, such as from approximately two days to approximately five days.
4. Glass transition temperature in the range approximately 25° C. to approximately 40° C., so that the material remains flexible and leathery in contact with the human body.
5. Hydrolytically unstable main chain structure, in order to ensure that the polymer breaks down after a predetermined period of time of application. For example, approximately 1 percent of the hydrolyzable bonds to be hydrolyzed in approximately 1 day, and approximately 10 percent cleavage in approximately 7 days. The rate of dissolution can accelerate because cleavage of hydrolysable bonds can lead to an increase in surface area.
6. Permeability to water and/or moisture of approximately $3{,}000\times10^{-13}$ to approximately $10{,}000\times10^{-13}$ $(cm^3)(cm)/(cm^2)(s)(cm\ Hg)$ at approximately 25° C.
7. Permeability to Oxygen: approximately $1\times10^{-13}$ to approximately $10\times10^{-13}(cm^3)(cm)/(cm^2)(s)(cm\ Hg)$, at approximately 25° C.
8. Ability to retard bacterial access or growth on the wound.
9. Ability to provide a scaffold for growth of new tissue.
10. Tensile Modulus at 50 percent elongation: approximately 50 psi to approximately 150 psi at approximately 25° C.
11. Elongation at break: approximately 50 percent to approximately 250 percent, such as approximately 100 to approximately 250 percent.

In addition, the material may be impregnated with drugs for delivery to the wound zone, and/or encapsulated so as to ensure a constant or predetermined rate and/or pattern of delivery.

A hydrogel or a polyacrylate bearing hydroxyl groups such as Poly (hydroxyethyl methacrylate) crosslinked with bisacrylamide (Poly-HEMA) can demonstrate many of these properties. A hydroxylated acrylate or methacrylate, such as hydroxyethyl methacrylate or glyceryl monomethacrylate) copolymerized with an acrylic terminated aliphatic main chain ether or carbonate or a polysaccharide can also have the ability to gradually disintegrate in contact with atmospheric moisture, or moisture exuded by the wound. This monofunctional acrylate can be further copolymerized with a multifunctional hydrophilic acrylate (such as 1, 3-propane diol diacrylate) in order to develop cross linking.

In certain exemplary embodiments, the precise formulation can be dependent upon the type of application or group of applications. For example, for treatment of chronic wounds (e.g., those suffered by advanced diabetic patients), it can be desirable to develop a material that will provide protection from bacterial infection for up to seven days. In this case, the hydrolytically unstable main-chain polymer can be selected to erode only in the presence of warm water that is applied to remove the dressing when desired. On the other hand, in case of burn victims, the dressing can be absorbable by the body, so that new layers of wound covering materials can be applied without having to remove the existing layer that might be supporting new tissue growth. Wound covers for these applications can exclude acrylates or methacrylates beyond a relatively minor fraction (less than approximately 25 percent) because they are not generally bioabsorbable. However, wound covering materials made entirely of absorbable materials will not necessarily meet the other properties listed above. For example, such materials are generally not elastomeric, and therefore can be quite rigid, and can be fracture prone and/or not able to be stretched. The permeability of these materials to moisture and oxygen are also not very high. A small fraction of acrylates or methacrylates (approximately 10 to approximately 25 percent by weight) therefore can be used to provide the desired permeability and physical properties (e.g., ability of being stretched) of the wound covering material. Since these wound covering materials can be absorbed by the body, it can be desirable that the acrylate or methacrylate fraction does not interfere with the healing process, since they can gradually accumulate in the wound area as more layers of wound healing materials are applied to the wound.

In general, three classes of wound healing materials can be developed for different types of application:
 a. Materials containing an erodable fraction can be removed via washing with warm water.
 b. Materials that are capable of being eroded by the natural moisture generated by the body, and are either wholly or mainly absorbed by the body.
 c. Materials that are removable via other methods.

Wound covering materials can be applied in various forms. In many cases, a scaffold of fabric can be covered with multiple layers of the wound healing material to provide more strength and durability to the dressing. In other cases, the material can be suspended in water in the form of latex, and applied by a spray or in the form of a paint.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of the appended claims. For example, regardless of the content of any portion (e.g., title, field, background, summary, abstract, drawing figure, etc.) of this application, unless clearly specified to the contrary, there is no requirement for the inclusion in any claim of the application of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc. Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, then any such conflicting information in such incorporated by reference material is specifically not incorporated by reference herein.

What is claimed is:

1. A composition prepared from a plurality of materials comprising a multifunctional hydrophilic monomer with 2 or more functionalities, and comprising at least 2 acrylic groups but less than 5 acrylic groups and not more than 11 hydroxyl groups, a processing aid comprising a soybean protein composition, and a polyethoxy methacrylate, said multifunctional hydrophilic monomer contributing approximately 0.1 percent to approximately 10 percent by dry weight of said composition, said processing aid contributing approximately 1 percent to approximately 10 percent by dry weight of said composition, and said polyethoxy methacrylate contributing an amount up to a balance by dry weight of said composition, wherein the composition releases heat when an ambient temperature is about 5° C. to about −15° C.

2. The composition of claim 1, wherein the composition is biodegradable.

3. The composition of claim 1, wherein the composition comprises particles.

4. The composition of claim 1, wherein the composition comprises solid particles.

5. The composition of claim 1, wherein the composition comprises nanoparticles.

6. The composition of claim 1, wherein the composition comprises particles having a molecular weight of from about 20,000 to about 50,000,000.

7. The composition of claim 1, wherein the composition comprises particles having an average diameter of from about 2 nanometers to about 1000 nanometers.

8. The composition of claim 1, wherein the composition comprises particles having an average diameter of from about 200 nanometers to about 500 nanometers.

9. The composition of claim 1, wherein the composition comprises particles having an average diameter of from about 100 nanometers to about 200 nanometers.

10. The composition of claim 1, wherein the composition comprises particles having an average diameter of from about 2 nanometers to about 200 nanometers.

11. The composition of claim 1, wherein the composition comprises particles having an average diameter of less than about 1000 nanometers.

12. The composition of claim 1, wherein the composition comprises particles having an average diameter of less than about 500 nanometers.

13. The composition of claim 1, wherein the composition comprises particles having an average diameter of less than about 200 nanometers.

14. The composition of claim 1, wherein the composition releases heat when an ambient temperature is about 3° C. to about −14° C.

15. The composition of claim 1, wherein the composition releases heat when an ambient temperature is about 1° C. to about −15° C.

16. The composition of claim 1, wherein the composition releases heat when an ambient temperature is less than about −5° C.

17. The composition of claim 1, wherein the composition releases heat when an ambient temperature is less than about −10° C.

18. A mixture comprising a polymer composition prepared from a plurality of materials comprising a multifunctional hydrophilic monomer with 2 or more functionalities, and comprising at least 2 acrylic groups but less than 5 acrylic groups and not more than 11 hydroxyl groups, a processing aid comprising a soybean protein composition, and a polyethoxy methacrylate, said multifunctional hydrophilic monomer contributing approximately 0.1 percent to approximately 10 percent by dry weight of said polymer composition, said processing aid contributing approximately 1 percent to approximately 10 percent by dry weight of said polymer composition, and said polyethoxy methacrylate contributing up to a balance by dry weight of said polymer composition, wherein the composition releases heat when an ambient temperature is about 5° C. to about −15° C.

19. The mixture of claim 18, further comprising water.

20. The mixture of claim 18, further comprising water, said water contributing approximately 90 percent to approximately 99.5 percent of a total weight of said mixture.

21. The mixture of claim 18, further comprising one or more components selected from a group comprising micronutrients, macronutrients, pesticides, insecticides, herbicides, rodenticides, fungicides, biocides, plant growth regulators, fertilizers, microbes, soil additives, adhesion promoting-agents, surfactants, and freezing point modifiers.

22. A method comprising a plurality of activities comprising:
providing a mixture comprising water and a composition prepared from a multifunctional hydrophilic monomer with 2 or more functionalities, and comprising at least 2 acrylic groups but less than 5 acrylic groups and not more than 11 hydroxyl groups a processing aid comprising a soybean protein composition, and a polyethoxy methacrylate, said multifunctional hydrophilic monomer contributing approximately 0.1 percent to approximately 10 percent by dry weight of said composition, said processing aid contributing approximately 1 percent to approximately 10 percent by dry weight of said composition, and said polyethoxy methacrylate contributing an amount up to a balance by dry weight of said composition, wherein the composition releases heat when an ambient temperature is about 5° C. to about −15° C.; and
coating at least a portion of a surface of an object with the mixture.

23. The method of claim 22, wherein the object is a plant material.

24. The method of claim 22, wherein the object is a human.

25. The method of claim 22, wherein the surface is human skin.

26. The method of claim 22, wherein the object is an animal.

27. The method of claim 22, further comprising spraying the mixture toward the surface.

28. The method of claim 22, further comprising preventing formation of ice on the surface.

29. The method of claim 22, further comprising preventing dehydration from the object.

30. The method of claim 22, further comprising reducing dehydration from the object.

31. The method of claim 22, further comprising reducing heat transfer via the surface.

32. The method of claim 22, further comprising reducing mass transfer via the surface.

33. The method of claim 22, further comprising reducing kinetic energy transfer to the object.

* * * * *